United States Patent
Patel et al.

(10) Patent No.: US 10,669,224 B2
(45) Date of Patent: Jun. 2, 2020

(54) HIGH-PURITY DIBASIC ACID COMPOSITIONS AND METHODS OF MAKING THE SAME

(71) Applicant: Elevance Renewable Sciences, Inc., Woodridge, IL (US)

(72) Inventors: Alpeshkumar K. Patel, Glendale Heights, IL (US); Brian Pease, Aurora, IL (US); Bradon J. Dreyer, Woodridge, IL (US); Yenamandra Viswanath, Naperville, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

(21) Appl. No.: 15/899,015

(22) Filed: Feb. 19, 2018

(65) Prior Publication Data

US 2018/0273461 A1    Sep. 27, 2018

Related U.S. Application Data

(63) Continuation of application No. 15/287,986, filed on Oct. 7, 2016, now Pat. No. 9,926,255, which is a continuation of application No. 14/502,382, filed on Sep. 30, 2014, now Pat. No. 9,487,463.

(60) Provisional application No. 61/888,440, filed on Oct. 8, 2013.

(51) Int. Cl.
| | | |
|---|---|---|
| C07C 51/43 | (2006.01) | |
| C07C 67/303 | (2006.01) | |
| C07C 67/475 | (2006.01) | |
| C07C 51/09 | (2006.01) | |

(52) U.S. Cl.
CPC ............. *C07C 51/43* (2013.01); *C07C 51/09* (2013.01); *C07C 67/303* (2013.01); *C07C 67/475* (2013.01)

(58) Field of Classification Search
CPC ....... C07C 51/43; C07C 51/09; C07C 67/475; C07C 67/303; C07C 55/02; C07C 69/34; C07C 69/593; C07C 51/48
See application file for complete search history.

(56) References Cited

U.S. PATENT DOCUMENTS

| | | | |
|---|---|---|---|
| 2,968,674 A | * | 1/1961 | Franke .................... C07C 51/09 |
| | | | 560/127 |
| 3,417,138 A | | 12/1968 | Amir et al. |
| 3,627,825 A | | 12/1971 | Davis |
| 5,563,294 A | | 10/1996 | Holzhauer et al. |
| 9,487,463 B2 | | 11/2016 | Patel et al. |
| 9,926,255 B2 | | 3/2018 | Patel et al. |
| 2009/0264672 A1 | | 10/2009 | Abraham et al. |
| 2013/0085288 A1 | | 4/2013 | Snead et al. |
| 2013/0204022 A1 | | 8/2013 | Snead et al. |
| 2014/0121402 A1 | | 5/2014 | Snead et al. |

FOREIGN PATENT DOCUMENTS

GB    2001312    1/1979

OTHER PUBLICATIONS

Weedon (Cartenoids and Related Compounds. Part V. Synthesis of Corticrocin, JACS 4168-4174, published 1954) (Year: 1954).*
Int'l Search Report & Written Opinion of Int'l Searching Authority for PCT App. No. PCT/US2014/058359, dated Mar. 17, 2015, 15 pages.
Int'l Preliminary Report on Patentability for PCT App. No. PCT/US2014/058359, dated Apr. 12, 2016, 11 pages.

* cited by examiner

*Primary Examiner* — Yevgeny Valenrod
*Assistant Examiner* — Blaine G Doletski
(74) *Attorney, Agent, or Firm* — Kilpatrick Townsend & Stockton LLP

(57) ABSTRACT

High-purity dibasic acid compositions are generally disclosed. In some embodiments, the dibasic acid compositions are solutions or suspensions. In some other embodiments, the compositions are solid-state compositions. In some such embodiments, the solid-state compositions include a dibasic acid as a crystalline solid and further include a low quantity of certain impurities, such as monobasic acids, various esters, and the like. Methods and systems for making such high-purity dibasic acid compositions are also disclosed.

16 Claims, 10 Drawing Sheets

HIGH-PURITY DIBASIC ACID COMPOSITIONS AND METHODS OF MAKING THE SAME

CROSS-REFERENCE TO RELATED APPLICATIONS

The present application is a continuation application of U.S. patent application Ser. No. 15/287,986, filed Oct. 7, 2016, which is a continuation of U.S. patent application Ser. No. 14/502,382, filed Sep. 30, 2014, which claims the benefit of priority of U.S. Provisional Application No. 61/888,440, filed Oct. 8, 2013. The contents of each of the foregoing applications are hereby incorporated by reference as though set forth herein in their entirety.

TECHNICAL FIELD

High-purity dibasic acid compositions are generally disclosed. In some embodiments, the dibasic acid compositions are solutions or suspensions. In some other embodiments, the compositions are solid-state compositions. In some such embodiments, the solid-state compositions comprise a dibasic acid as a crystalline solid and further comprise a low quantity of certain impurities, such as monobasic acids, various esters, and the like. Methods and systems for making such high-purity dibasic acid compositions are also disclosed.

BACKGROUND

Dibasic acids are organic compounds having two carboxylic acid groups. Such compounds can be used in a wide array of different ways. Because of their difunctionality, they are commonly used in making certain polymers. For example, a polyamide can be made by reacting a dibasic acid with a diamine, i.e., an organic compound having two amine groups. As another example, a polyester can be made by reacting a dibasic acid with a diol, i.e., an organic compound having two hydroxyl groups.

In certain instances, it may be desirable to use dibasic acids in a highly pure form, as the presence of impurities may cause certain undesirable events to occur. For example, if a dibasic acid composition contains a substantial amount of monobasic acid impurity, it can cause early chain termination in the polymerization process, thereby resulting in polymer chains that may have a lower molecular weight than desired.

Thus, there is a continuing need to develop cost-effective and scalable methods of making dibasic acids that result in high-purity compositions, especially compositions that have a low concentration of monobasic acid impurity.

SUMMARY

In a first aspect, the disclosure provides methods for hydrolyzing a dibasic ester, including: introducing a dibasic ester to a reactor; and reacting the dibasic ester with water in the reactor at an elevated temperature to form a dibasic acid and an alcohol; wherein at least a portion of the formed alcohol is removed from the reactor during the reacting step.

In a second aspect, the disclosure provides methods of hydrolyzing a dibasic ester, including: introducing a first composition to a reactor, the first composition comprising at least 50 grams of dibasic ester; and reacting the dibasic ester in the reactor with water to form a second composition comprising a dibasic acid; wherein the second composition is substantially free of colored impurities.

In a third aspect, the disclosure provides hydrolysis reactors, including: a pressurizable vessel disposed proximate to a heat source, wherein the pressurizable vessel comprises an inlet and a an outlet; a water source, wherein the water source is in fluid communication with the liquid inlet of the pressurizable vessel; and a condenser, wherein the condenser is in fluid communication with the gas outlet of the pressurizable vessel via an adjustable pressure regulator disposed between the condenser and the gas outlet.

In a fourth aspect, the disclosure provides methods of forming a purified solid-state dibasic acid composition, including: providing a first composition, which comprises a first amount of dibasic acid and a first amount of one or more monobasic acids, each dissolved in a solvent system; and cooling the first composition to form a second composition, which comprises a second amount the dibasic acid in solid-state form suspended in the solvent system, and a second amount of the one or more monobasic acids dissolved in the solvent system.

In a fifth aspect, the disclosure provides methods of forming a dibasic acid, including: reacting a first olefin ester and an second olefin ester in the presence of a metathesis catalyst to form a first alkene and an unsaturated dibasic ester; hydrogenating the unsaturated dibasic ester to form a saturated dibasic ester; and converting the saturated dibasic ester to a saturated dibasic acid. In some embodiments, the first olefin ester and the second olefin ester are the same compound. In some other embodiments, the first olefin ester and the second olefin ester are different compounds. In some such embodiments, the first olefin ester is a terminal olefin ester and the second olefin ester is an internal olefin ester.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative, and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 1:
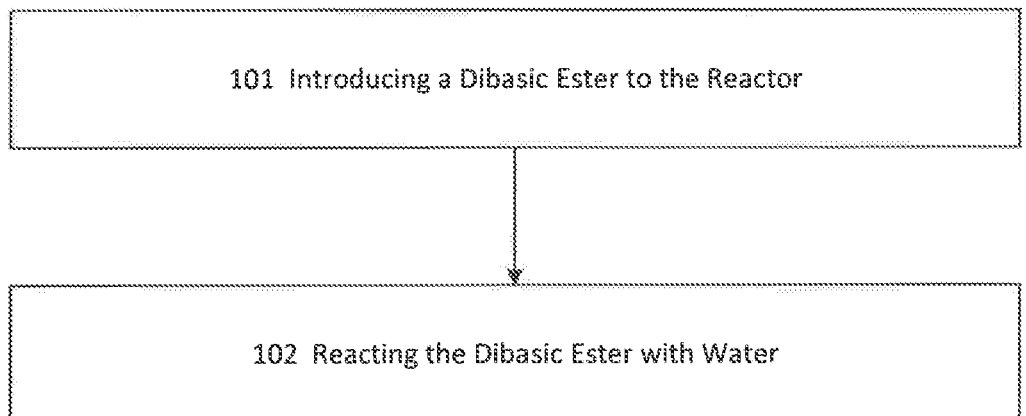
FIG. 1 shows an illustrative embodiment of a method for hydrolyzing a dibasic ester to a dibasic acid.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9, 12-octadecadienoic acid), and linolenic acid (9,12,15-octadecatrienoic acid).

As used herein, "metathesis catalyst" includes any catalyst or catalyst system that catalyzes an olefin metathesis reaction.

As used herein, "metathesize" or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin metathesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, "hydrocarbon" refers to an organic group composed of carbon and hydrogen, which can be saturated or unsaturated, and can include aromatic groups. The term "hydrocarbyl" refers to a monovalent or polyvalent hydrocarbon moiety.

As used herein, "olefin" or "olefins" refer to compounds having at least one unsaturated carbon-carbon double bond. In certain embodiments, the term "olefins" refers to a group of unsaturated carbon-carbon double bond compounds with different carbon lengths. Unless noted otherwise, the terms "olefin" or "olefins" encompasses "polyunsaturated olefins" or "poly-olefins," which have more than one carbon-carbon double bond. As used herein, the term "monounsaturated olefins" or "mono-olefins" refers to compounds having only one carbon-carbon double bond. A compound having a terminal carbon-carbon double bond can be referred to as a "terminal olefin," while an olefin having a non-terminal carbon-carbon double bond can be referred to as an "internal olefin."

As used herein, the term "low-molecular-weight olefin" may refer to any one or combination of unsaturated straight, branched, or cyclic hydrocarbons in the $C_{2-14}$ range. Low-molecular-weight olefins include "alpha-olefins" or "terminal olefins," wherein the unsaturated carbon-carbon bond is present at one end of the compound. Low-molecular-weight olefins may also include diener or trienes. Low-molecular-weight olefins may also include internal olefins or "low-molecular-weight internal olefins." In certain embodiments, the low-molecular-weight internal olefin is in the $C_{4-14}$ range. Examples of low-molecular-weight olefins in the $C_{2-6}$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_{7-9}$ range include 1,4-heptadiene, 1-heptene, 3,6-nonadiene, 3-nonene, 1,4,7-octatriene. Other possible low-molecular-weight olefins include styrene and vinyl cyclohexane. In certain embodiments, it is preferable to use a mixture of olefins, the mixture comprising linear and branched low-molecular-weight olefins in the $C_{4-10}$ range. In one embodiment, it may be preferable to use a mixture of linear and branched $C_4$ olefins (i.e., combinations of: 1-butene, 2-butene, and/or isobutene). In other embodiments, a higher range of $C_{11-C14}$ may be used.

In some instances, the olefin can be an "alkene," which refers to a straight- or branched-chain non-aromatic hydrocarbon having 2 to 30 carbon atoms and one or more carbon-carbon double bonds, which may be optionally substituted, as herein further described, with multiple degrees of substitution being allowed. A "monounsaturated alkene" refers to an alkene having one carbon-carbon double bond, while a "polyunsaturated alkene" refers to an alkene having two or more carbon-carbon double bonds. A "lower alkene," as used herein, refers to an alkene having from 2 to 10 carbon atoms.

As used herein, "alpha-olefin" refers to an olefin (as defined above) that has a terminal carbon-carbon double bond. In some embodiments, the alpha-olefin is a terminal alkene, which is an alkene (as defined above) having a terminal carbon-carbon double bond. Additional carbon-carbon double bonds can be present.

As used herein, "ester" or "esters" refer to compounds having the general formula: R—COO—R', wherein R and R' denote any organic group (such as alkyl, aryl, or silyl groups) including those bearing heteroatom-containing substituent groups. In certain embodiments, R and R' denote alkyl, alkenyl, aryl, or alcohol groups. In certain embodiments, the term "esters" may refer to a group of compounds with the general formula described above, wherein the compounds have different carbon lengths. In certain embodiments, the esters may be esters of glycerol, which is a trihydric alcohol. The term "glyceride" can refer to esters where one, two, or three of the —OH groups of the glycerol have been esterified. Thus, the term "unsaturated glyceride" can refer to monoglycerides, diglycerides, or triglycerides, where one or more of the acid portions of the ester contain unsaturation, e.g., a carbon-carbon double bond.

It is noted that an olefin may also comprise an ester, and an ester may also comprise an olefin, if the R or R' group in the general formula R—COO—R' contains an unsaturated carbon-carbon double bond. Such compounds can be referred to as "olefin esters." Further, a "terminal olefin ester" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, or silyl group) and R has an olefin positioned at the end of the chain, and the term "internal olefin" may refer to an ester or an acid thereof where R' denotes hydrogen or any organic compound (such as an alkyl, aryl, or silyl group) and R has an olefin positioned at an internal location on the chain.

As used herein, "acid" or "acids" refer to compounds having the general formula: R—COOH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "acids" may refer to a group of compounds with the general formula described above, wherein the compounds have different carbon lengths. The term "carboxyl" refers to a —COOH moiety. The term "carboxylated" refers to a "carboxyl" group formed on another group or compound.

As used herein, the term "dibasic ester" may refer to compounds having the general formula R—OOC—Y—COO—R', wherein Y, R, and R' denote any organic compound (such as alkyl, aryl, or silyl groups), including those bearing heteroatom containing substituent groups. In certain embodiments, Y is a saturated or unsaturated hydrocarbon, and R and R' are alkyl or alkenyl groups. In instances where Y is a saturated hydrocarbon, the dibasic ester can be referred to as a "saturated dibasic ester." In instances where Y is an unsaturated hydrocarbon, the dibasic ester can be referred to as an "unsaturated dibasic ester."

As used herein, the term "dibasic acid" may refer to compounds having the general formula R—OOC—Y—COO—R', wherein R and R' are hydrogen atoms, and Y denotes any organic compound (such as an alkyl, aryl, or silyl group), including those bearing heteroatom substituent groups. In certain embodiments, Y is a saturated or unsaturated hydrocarbon. In instances where Y is a saturated hydrocarbon, the dibasic acid can be referred to as a "saturated dibasic acid." In instances where Y is an unsaturated hydrocarbon, the dibasic acid can be referred to as an "unsaturated dibasic acid."

As used herein, "alcohol" or "alcohols" refer to compounds having the general formula: R—OH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "alcohol" or "alcohols" may refer to a group of compounds with the general formula described above, wherein the compounds have different carbon lengths. The term "hydroxyl" refers to a —OH moiety.

As used herein, "amine" or "amines" refer to compounds having the general formula: R—N(R')(R"), wherein R, R', and R" denote a hydrogen or an organic moiety (such as alkyl, aryl, or silyl groups), including those bearing heteroatom-containing substituent groups. In certain embodiments, R, R', and R" denote a hydrogen or an alkyl, alkenyl, aryl, or alcohol groups. In certain embodiments, the term "amines" may refer to a group of compounds with the general formula described above, wherein the compounds have different carbon lengths. The term "amino" refers to a —N(R)(R') moiety.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number of carbon atoms in an alkyl group is represented by the phrase "$C_{x-y}$ alkyl," which refers to an alkyl group, as herein defined, containing from x toy, inclusive, carbon atoms. Thus, "$C_{1-6}$alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the "alkyl" group can be divalent, in which case the group can alternatively be referred to as an "alkylene" group. Also, in some instances, one or more of the carbon atoms in the alkyl or alkylene group can be replaced by a heteroatom (e.g., selected from nitrogen, oxygen, or sulfur, including N-oxides, sulfur oxides, and sulfur dioxides, where feasible), and is referred to as a "heteroalkyl" or "heteroalkylene" group, respectively. Non-limiting examples include "oxyalkyl" or "oxyalkylene" groups, which are groups of the following formulas: -[-(alkylene)-O-]$_x$-alkyl, or -[-(alkylene)-O-]$_x$-alkylene-, respectively, where x is 1 or more, such as 1, 2, 3, 4, 5, 6, 7, or 8.

As used herein, "alkenyl" refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. The number of carbon atoms in an alkenyl group is represented by the phrase "$C_{x-y}$ alkenyl," which refers to an alkenyl group, as herein defined, containing from x to y, inclusive, carbon atoms. Thus, "$C_{2-6}$ alkenyl" represents an alkenyl chain having from 2 to 6 carbon atoms and, for example, includes, but is not limited to, ethenyl, 2-propenyl, 2-butenyl, and 3-butenyl. In some instances, the "alkenyl" group can be divalent, in which case the group can alternatively be referred to as an "alkenylene" group. Also, in some instances, one or more of the saturated carbon atoms in the alkenyl or alkenylene group can be replaced by a heteroatom (e.g., selected from nitrogen, oxygen, or sulfur, including N-oxides, sulfur oxides, and sulfur dioxides, where feasible), and is referred to as a "heteroalkenyl" or "heteroalkenylene" group, respectively.

As used herein, "alkynyl" refers to a straight or branched chain non-aromatic hydrocarbon having 2 to 30 carbon atoms and having one or more carbon-carbon triple bonds, which may be optionally substituted, as herein further described, with multiple degrees of substitution being allowed. Examples of "alkynyl," as used herein, include, but are not limited to, ethynyl, 2-propynyl, 2-butynyl, and 3-butynyl. The number of carbon atoms in an alkynyl group is represented by the phrase "$C_{x-y}$ alkynyl," which refers to an alkynyl group, as herein defined, containing from x toy, inclusive, carbon atoms. Thus, "$C_{2-6}$alkynyl" represents an alkynyl chain having from 2 to 6 carbon atoms and, for example, includes, but is not limited to, ethynyl, 2-propynyl, 2-butynyl, and 3-butynyl. In some instances, the "alkynyl" group can be divalent, in which case the group can alternatively be referred to as an "alkynylene" group. Also, in some instances, one or more of the saturated carbon atoms in the alkynyl group can be replaced by a heteroatom (e.g., selected from nitrogen, oxygen, or sulfur, including N-oxides, sulfur oxides, and sulfur dioxides, where feasible), and is referred to as a "heteroalkynyl" group.

As used herein, "cycloalkyl" refers to an aliphatic saturated or unsaturated hydrocarbon ring system having 1 to 20 carbon atoms, which may be optionally substituted, as herein further described, with multiple degrees of substitution being allowed. Examples of "cycloalkyl," as used herein, include, but are not limited to, cyclopropyl, cyclobutyl, cyclopentyl, cyclohexyl, cyclohexenyl, cycloheptyl, cyclooctyl, adamantyl, and the like. The number of carbon atoms in a cycloalkyl group is represented by the phrase "$C_{x-y}$ alkyl," which refers to a cycloalkyl group, as herein defined, containing from x to y, inclusive, carbon atoms. Thus, "$C_{3-10}$ cycloalkyl" represents a cycloalkyl having from 3 to 10 carbon atoms and, for example, includes, but is not limited to, cyclopropyl, cyclobutyl, cyclopentyl, cyclohexyl, cyclohexenyl, cycloheptyl, cyclooctyl, and adamantyl. In some instances, the "cycloalkyl" group can be divalent, in which case the group can alternatively be referred to as a "cycloalkylene" group. Also, in some instances, one or more of the carbon atoms in the cycloalkyl or cycloalkylene group can be replaced by a heteroatom (e.g., selected from nitrogen, oxygen, or sulfur, including N-oxides, sulfur oxides, and sulfur dioxides, where feasible), and is referred to as a "heterocycloalkyl" or "heterocycloalkylene" group, respectively.

As used herein, "alkoxy" refers to —OR, where R is an alkyl group (as defined above). The number of carbon atoms in an alkyl group is represented by the phrase "$C_{x-y}$ alkoxy," which refers to an alkoxy group having an alkyl group, as herein defined, containing from x to y, inclusive, carbon atoms.

As used herein, "halogen" or "halo" refers to a fluorine, chlorine, bromine, and/or iodine atom. In some embodiments, the terms refer to fluorine and/or chlorine. As used herein, "haloalkyl" or "haloalkoxy" refer to alkyl or alkoxy groups, respectively, substituted by one or more halogen atoms. The terms "perfluoroalkyl" or "perfluoroalkoxy" refer to alkyl groups and alkoxy groups, respectively, where every available hydrogen is replaced by fluorine.

As used herein, "substituted" refers to substitution of one or more hydrogen atoms of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, "yield" refers to the amount of reaction product formed in a reaction. When expressed with units of percent (%), the term yield refers to the amount of reaction product actually formed, as a percentage of the amount of reaction product that would be formed if all of the limiting reactant were converted into the product.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Other terms are defined in other portions of this description, even though not included in this subsection.

Hydrolysis of Dibasic Esters

In certain aspects, the disclosure provides methods for hydrolyzing a dibasic ester, comprising: introducing a dibasic ester to a reactor; and reacting the dibasic ester with water in the reactor to form a dibasic acid and an alcohol.

The methods include introducing a dibasic ester to a reactor. The acid can be introduced in any suitable manner. For example, in some embodiments, the dibasic ester is added to the reactor, either alone or with other ingredients. In some other embodiments, however, the dibasic acid is generated in the reactor, for example, as the product of a chemical reaction that occurs in the reactor. The dibasic ester can be in any suitable form, for example, as a solid, in a slurry with a suitable liquid carrier, in a suspension with a suitable liquid carrier, or dissolved in a solvent. In some embodiments, the dibasic acid is introduced to the reactor as a solid composition. In some other embodiments, the dibasic ester is introduced to the reactor dissolved in a solution. Any suitable solvent system can be used for the solution, including, but not limited to, solvent systems that include ethyl acetate, acetonitrile, heptane, hexane, diethyl ether, methyl tert-butyl ether (MBTE), petroleum ether, toluene, ortho-xylene, meta-xylene, para-xylene, acetone, dimethylformamide, tetrahydrofuran, methylene dichloride, 1-butanol, isopropyl alcohol, isopropyl acetate, 1,2-dimethoxyethane, and dimethyl sulfoxide. In some embodiments, the solvent system comprises toluene. In some embodiments, these solvent systems can include compounds that are miscible with water. In some embodiments, these solvent systems can include compounds that are not miscible with water. In some embodiments, these solvent systems can include one or more compounds that are not miscible with water and one or more compounds that are miscible in water.

In some embodiments, the composition can also include other organic esters, such as monobasic esters, but in smaller relative quantities than the dibasic ester. In some embodiments, these monobasic esters can include esters of various saturated fatty acids. These include, but are not limited to, esters of hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, and the like. In some embodiments, these monobasic esters can include esters of various unsaturated fatty acids, such as esters of octenoic acid, nonenoic acid, decenoic acid, undecenoic acid, dodecenoic acid, tridecenoic acid, tetradecenoic acid, pentadecenoic acid, hexadecenoic acid, heptadecenoic acid, octadecenoic acid, tridecadienoic acid, hexadecadienoic acid, and the like. In some embodiments, such esters are esters of simple aliphatic alcohols, such as methyl esters, ethyl esters, or isopropyl esters, of any of the aforementioned acids.

In some embodiments, the dibasic ester can be formed by a process that includes self-metathesizing an unsaturated ester or cross-metathesizing two or more unsaturated esters. In such embodiments, the composition can include small quantities of the saturated (e.g., hydrogenated) variants of the unsaturated esters used as reactants in the metathesis. The composition can also include other saturated (e.g., hydrogenated) mono-ester byproducts of the metathesis reaction, e.g., from the non-productive metathesis of the reactants with various alkenes and olefinic esters formed in the metathesis reactor.

In some embodiments, the dibasic ester is disposed in the reactor as a component of a composition. In some embodiments, the composition also includes water or a substance that can release water. In some embodiments, the composition also includes an acid, such as a Bronstead or Lewis acid, which can serve to catalyze the reaction of the dibasic ester with the water. Any suitable acid or combination of acids can be used. In some embodiments, for example, the acid is a water-soluble acid, such as a water-soluble Bronstead acid. In some embodiments, the acid is a water-soluble organic acid. In some other embodiments, the acid is a water-soluble inorganic acid. Suitable inorganic acids include, but are not limited to: hydrohalic acids, such as hydrofluoric acid, hydrochloric acid, hydrobromic acid, and the like; other halogen-containing acids, such as perchloric acid, chloric acid, hypochlorous acid, hypofluorous acid, and the like; nitrogen-containing acids, such as nitric acid, nitrous acid, and the like; phosphorus-containing acids, such as phosphoric acid (as well as dihydrogen phosphates and hydrogen phosphates), phosphorous acid (as well as hydrogen phosphites), hypophosphorous acid, and the like; boron-containing acids, such as boric acid and the like; and sulfur-containing acids, such as sulfuric acid (as well as hydrogen sulfates), sulfurous acid (as well as hydrogen sulfites), and the like. Suitable organic acids include, but are not limited to, substituted and unsubstituted hydrocarbyl groups having a carboxylic acid group, a phenolic group, a sulfonic acid group, or other like groups. In some embodiments, no additional acid is added. In such embodiments, the formed dibasic acid can catalyze the reaction, although, in some embodiments, a small amount of the dibasic acid to be formed can be used to seed the process. Further, in embodiments where the composition in the reactor comprises one or more acids, one or more of those acids can be homogeneous, meaning that they are at least partially solubilized by a liquid carrier (e.g., a solvent system). In some other embodiments, however, one or more of the acids are heterogeneous, meaning that they are not solubilized by any liquid carrier. For example, in some such embodiments, one or more of the acids can be disposed on a solid support, such as a polymeric support (e.g., polystyrene and the like) or an inorganic support (e.g., silica, alumina, and the like).

The method is not limited to any particular dibasic ester. In some embodiments, the dibasic ester is a compound having the formula: R—OOC—Y—COO—R', wherein Y, R, and R' denote any organic compound (such as hydrocarbyl or silyl groups), including those bearing heteroatom containing substituent groups. In some such embodiments, R and R' are independently hydrocarbyl groups, which can be optionally substituted with various heteroatom-containing substituents, or whose carbon atoms can be replaced by one or more heteroatoms. Such hydrocarbyl groups can include substituted and unsubstituted alkyl, alkenyl, and oxyalkyl groups. In some such embodiments, Y is a divalent hydrocarbyl group, which can be optionally substituted with various heteroatom-containing substituents, or whose carbon atoms can be replaced by one or more heteroatoms. Such divalent hydrocarbyl groups can include substituted and unsubstituted alkylene, alkenylene, and oxyalkylene groups.

In some embodiments, the dibasic ester is a compound of formula (I):

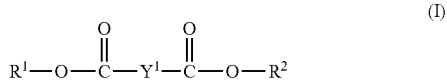

wherein, $Y^1$ is $C_{6-36}$ alkylene, $C_{6-36}$ alkenylene, $C_{6-36}$ heteroalkylene, or $C_{6-36}$ heteroalkenylene, each of which is optionally substituted one or more times by substituents selected independently from $R^3$;

$R^1$ and $R^2$ are independently $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^3$; and $R^3$ is a halogen atom, —OH, —NH$_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some embodiments, $Y^1$ is $C_{6-36}$ alkylene, $C_{6-36}$ alkenylene, or $C_{4-36}$ oxyalkylene, each of which is optionally substituted one or more times by substituents selected from the group consisting of a halogen atom, —OH, —O($C_{1-6}$ alkyl), —NH$_2$, —NH($C_{1-6}$ alkyl), and N($C_{1-6}$alkyl)$_2$. In some further such embodiments, $Y^1$ is $C_{6-36}$ alkylene, $C_{6-36}$ alkenylene, or $C_{4-36}$ oxyalkylene, each of which is option-ally substituted one or more times by —OH. In some further such embodiments, $Y^1$ is —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{17}$—, —(CH$_2$)$_{18}$—, —(CH$_2$)$_{19}$—, —(CH$_2$)$_{20}$—, —(CH$_2$)$_{21}$—, or —(CH$_2$)$_{22}$—. In some embodiments, $Y^1$ is —(CH$_2$)$_9$—. In some embodiments, $Y^1$ is —(CH$_2$)$_{12}$—. In some embodiments, $Y^1$ is —(CH$_2$)$_{16}$—.

In some embodiments, $R^1$ and $R^2$ are independently $C_{1-8}$ alkyl, $C_{2-8}$ alkenyl, or $C_{1-8}$ oxyalkenyl, each of which is optionally substituted one or more times by —OH. In some further embodiments, $R^1$ and $R^2$ are independently methyl, ethyl, propyl, isopropyl, butyl, isobutyl, sec-butyl, tert-butyl, pentyl, tert-pentyl, neopentyl, hexyl, or 2-ethylhexyl. In some further embodiments, $R^1$ and $R^2$ are independently methyl, ethyl, or isopropyl. In some embodiments, $R^1$ and $R^2$ are both methyl.

In some embodiments, the dibasic ester is undecanedioic acid dimethyl ester. In some embodiments, the dibasic ester is tetradecanedioic acid dimethyl ester. In some embodiments, the dibasic ester is octadecanedioic acid dimethyl ester.

Any suitable amount of the dibasic ester can be disposed in the reactor. In some embodiments, at least 50 grams, or at least 100 grams, or at least 150 grams, or at least 200 grams, are introduced to the reactor.

Any suitable reactor can be used for introducing the dibasic ester. In some embodiments, the reactor is a pressurizable reactor. In some such embodiments, the reactor includes a sealable reaction vessel that can hold a pressure up to about 5 bar, or up to about 10 bar, or up to about 20 bar, or up to about 30 bar, or up to about 40 bar, or up to about 50 bar, or up to about 75 bar, or up to about 100 bar. In some embodiments, the reactor is equipped with a means of heating its contents. Thus, in some embodiments, the reactor can include one or more heating elements disposed proximate to the reaction vessel. Any suitable heating elements can be used, including, but not limited to, electric wires (e.g., electric heating coils), thermocouples, gas burners, heating blocks, pipes containing heated fluids (e.g., steam pipes, hot oil pipes, etc.), and the like. In some embodiments, one or more suitable heating elements can be included on the inside of the reaction vessel. In some embodiments, such internal heating elements can be the sole means used for heating the reactor contents. In other embodiments, however, such internal heating elements can be used in addition to one or more external heating elements. Because such internal heating elements may be in contact with the reactor contents, in some embodiments, the internal heating element is designed such that it can operate when in physical contact with one or more of the reactor contents. For example, in some embodiments, such internal heating elements include, but are not limited to, electric wires (e.g., electric heating coils), thermocouples, pipes containing heated fluids (e.g., steam pipes, hot oil pipes, etc.), and the like.

The reaction vessel can have any suitable volume and/or shape, depending on the certain factors, including, but not limited to, the nature of the reactants and products, the desired reaction temperature and pressure, the quantities of reactants. In some embodiments, the reaction vessel is a 600 mL Hastelloy C Parr reactor. In some other embodiments, the reaction vessel is a Hastelloy C pressure reactor, e.g., having a volume of 500 L to 9000 L.

In some embodiments, the reaction vessel can include various devices or structures to assist with fluid flow. Such devices or structures can include, but are not limited to, baffles, stirrers, stir bars, impellers, and the like. These elements can be disposed in the reactor in any suitable manner, depending on the desired reaction conditions, the nature of the reactor contents, and on other factors.

The reactor can also include various inlets and outlets for adding or removing fluids (including gases and/or liquids) from the reactor. In some embodiments, the reactor includes an inlet suitable for adding a liquid medium to the reactor. In some such embodiments, this liquid inlet is in fluid communication with a vessel containing said liquid medium. In some such embodiments, one or more pumps can be disposed between the liquid-containing vessel and the inlet. Any pumps suitable for pumping a liquid medium can be used. In some embodiments, the liquid medium is an aqueous medium, such as water. In some embodiments, the reactor includes an outlet suitable for removing a gaseous medium from the reaction vessel. In some embodiments, said gas outlet is in fluid communication with a receiving vessel. In some embodiments, the receiving vessel is a condenser, or is disposed proximate to one or more cooling elements, such that one or more of the substances contained in any gaseous stream can be condensed to a liquid. In some such embodiments, one or more pressure regulators are disposed between the receiving vessel and the gaseous outlet. Any suitable regulators can be used, so long as they can allow release of one or more gaseous species from the reactor without inducing a substantial reduction of reactor pressure. In some embodiments, the reactor may also include a gaseous inlet, such as a gaseous inlet that can be used for adding one or more gases (e.g., inert gases or non-reacting gases) to the reactor. Such an inlet can be used to sparge the reactor, e.g., during the course of the reaction. Or, in some other instances, it can be used to flush the reactor of undesired species, e.g., to flush the reactor of oxidants, such as oxygen. In some embodiments, the gas inlet is suitable for delivery of certain inert gases to the reactor, either before, during, and/or after the reaction. Such inert gases include, but are not limited to, nitrogen, helium, neon, argon, methane (flared), carbon dioxide, and the like.

The methods include reacting the dibasic ester with water in the reactor to form a dibasic acid and an alcohol. The dibasic ester can be a dibasic ester according to any of the above embodiments. Accordingly, in some embodiments, the resulting dibasic acid is a compound having the formula: H—OOC—Y—COO—H, wherein Y denotes any organic compound (such as hydrocarbyl or silyl groups), including those bearing heteroatom containing substituent groups. In some such embodiments, Y is a divalent hydrocarbyl group, which can be optionally substituted with various heteroatom-containing substituents, or whose carbon atoms can be replaced by one or more heteroatoms. Such divalent hydrocarbyl groups can include substituted and unsubstituted alkylene, alkenylene, and oxyalkylene groups. In some such embodiments, the reaction also yields one or more alcohols. In some embodiments, the alcohols are compounds having the formulas: R—OH and R'—OH, where R and R' denote any organic compound (such as hydrocarbyl or silyl groups), including those bearing heteroatom containing substituent groups. In some such embodiments, R and R' are independently hydrocarbyl groups, which can be optionally substituted with various heteroatom-containing substituents, or whose carbon atoms can be replaced by one or more heteroatoms. Such hydrocarbyl groups can include substituted and unsubstituted alkyl, alkenyl, and oxyalkyl groups.

In some embodiments, the reaction forms a dibasic acid of formula (II) and alcohols of formula (IIIa) and formula (IIIb):

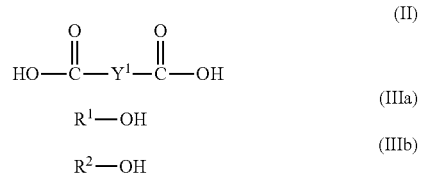

wherein, $Y^1$ is $C_{6-36}$ alkylene, $C_{6-36}$ alkenylene, $C_{6-36}$ heteroalkylene, or $C_{6-36}$ heteroalkenylene, each of which is optionally substituted one or more times by substituents selected independently from $R^3$;

$R^1$ and $R^2$ are independently $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^3$; and $R^3$ is a halogen atom, —OH, —$NH_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some embodiments, $Y^1$ is $C_{6-36}$ alkylene, $C_{6-36}$ alkenylene, or $C_{4-36}$ oxyalkylene, each of which is optionally substituted one or more times by substituents selected from the group consisting of a halogen atom, —OH, —O($C_{1-6}$ alkyl), —$NH_2$, —NH($C_{1-6}$ alkyl), and N($C_{1-6}$alkyl)$_2$. In some further such embodiments, $Y^1$ is $C_{6-36}$ alkylene, $C_{6-36}$ alkenylene, or $C_{4-36}$ oxyalkylene, each of which is optionally substituted one or more times by —OH. In some further such embodiments, $Y^1$ is —$(CH_2)_8$—, —$(CH_2)_8$—, —$(CH_2)_{10}$—, —$(CH_2)_{11}$—, —$(CH_2)_{12}$—, —$(CH_2)_{13}$—, —$(CH_2)_{14}$—, —$(CH_2)_{15}$—, —$(CH_2)_{16}$—, —$(CH_2)_{17}$—, —$(CH_2)_{18}$—, —$(CH_2)_{19}$—, —$(CH_2)_{20}$—, —$(CH_2)_{21}$—, or —$(CH_2)_{22}$—. In some embodiments, $Y^1$ is —$(CH_2)_9$—. In some embodiments, $Y^1$ is —$(CH_2)_{12}$—. In some embodiments, $Y^1$ is —$(CH_2)_{16}$—.

In some embodiments, $R^1$ and $R^2$ are independently $C_{1-8}$ alkyl, $C_{2-8}$ alkenyl, or $C_{1-8}$ oxyalkyl, each of which is optionally substituted one or more times by —OH. In some further embodiments, $R^1$ and $R^2$ are independently methyl, ethyl, propyl, isopropyl, butyl, isobutyl, sec-butyl, tert-butyl, pentyl, tert-pentyl, neopentyl, hexyl, or 2-ethylhexyl. In some further embodiments, $R^1$ and $R^2$ are independently methyl, ethyl, or isopropyl. In embodiments, $R^1$ and $R^2$ are both methyl.

In some embodiments, the dibasic acid is undecanedioic acid. In some embodiments, the dibasic ester is tetradecanedioic acid. In some embodiments, the dibasic ester is octadecanedioic acid. In some embodiments, the alcohols are selected from the group consisting of: methanol, ethanol, isopropanol, and mixtures thereof. In some such embodiments, the alcohols are both methanol.

The water used in the reaction can be any suitable form of water, including but not limited to, distilled water, deionized water, and the like. In some embodiments, deionized water is used. In some embodiments, an excess of water is used relative to the dibasic ester. In some embodiments, the initial mole-to-mole ratio of water to the dibasic acid in the reactor is from 1:1 to 25:1, or from 2:1 to 20:1, or from 3:1 to 15:1.

The reaction can be carried out in any suitable reactor and under any suitable conditions. In some embodiments, the reactor is a reactor according to any of the embodiments described above. In some embodiments, the reaction is carried out at an elevated temperature, e.g., at a temperature above 25° C. In some embodiments, the reaction is carried out at a temperature (or at temperatures) from 50° C. to 500°

C., or from 100° C. to 300° C., or from 150° C. to 300° C., or from 200° C. to 250° C. In some embodiments, the reaction is carried out at a temperature of about 225° C. In some embodiments, the reaction can be carried out at an elevated pressure, e.g., at a pressure above about 1 bar. In some embodiments, the reaction is carried out at a pressure of 1 barg to 50 barg, or from 10 barg to 40 barg. In some embodiments, the reaction is carried out at a pressure of about 25 barg. As used herein, the "barg" refers to the pressure in bar above atmospheric pressure. Thus, if atmospheric pressure is about 1 bar, then 25 barg roughly corresponds to 26 bar pressure. Further, the reaction can be carried out for any suitable duration, depending on a variety of factors, including, but not limited to, the reactor design, the quantity of material being reacted, the temperature, pressure, and the like. In some embodiments, the reaction time is 2 to 12 hours, or 4 to 10 hours. In some embodiments, the reaction duration is about 5 hours, or about 6 hours, or about 7 hours, or about 8 hours, or about 9 hours, or about 10 hours, or about 11 hours, or about 12 hours.

In some embodiments, various species can be added and/or removed during the course of the reaction, e.g., to maintain the pressure, to increase yield, etc. In some embodiments, an inert gas or non-reacting gas is added during the course of the reaction. Suitable inert gases include, but are not limited to, gases that are non-condensing under typical reaction conditions, such as nitrogen, helium, neon, argon, methane (flared), carbon dioxide, or mixtures thereof. The addition can be carried out in various ways. For example, in some embodiments, the addition can be carried out in one or more discontinuous intervals. Or, in some other embodiments, the addition can be carried out continuously. Any suitable flow rate can be used. For example, in some embodiments, the inert gas can be continuously supplied to the reactor at a flow rate of 100 to 2000 sccm, or from 250 to 1500 sccm. Note, as used herein, "sccm" refers to standard cubic centimeters per minute, where the standard is at 21° C. and 1 atm pressure). In some embodiments, the flow rate can be set to achieve a certain residence time under the given reaction conditions (e.g., temperature, pressure, etc.). In some such embodiments, the residence time of the added gas is from 10 minutes to 24 hours, or 10 minutes to 12 hours, or 10 minutes to 4 hours, or 10 to 60 minutes. In some embodiments, the added gas is permanently present during the reaction.

In some embodiments, additional water can be added during the course of the reaction. The addition can be carried out in various ways. For example, in some embodiments, the addition can be carried out in one or more discontinuous intervals. Or, in some other embodiments, the addition can be carried out continuously. Any suitable amount of water can be added to the reactor during the course of the reaction. As discussed in more detail below, in some embodiments, an amount of the formed alcohols is removed from the reactor during the course of the reaction. In some such embodiments, the amount of water added to the reactor during the course of the reaction is the amount of water (e.g., mass of water) approximately equivalent to the total mass of the alcohols removed from the reactor during the course of the reaction. For example, in some embodiments, the mass-to-mass ratio of water added to the reactor during the course of the reaction to alcohol removed from the reactor during the course of the reaction is from 0.7:1 to 1.3 to 1, or from 0.8:1 to 1.2:1, or from 0.9:1 to 1.1:1. In some embodiments, the ratio is about 1:1. The water can be added in any suitable manner. In embodiments where the reactor includes a liquid inlet (described above), the water is, in some such embodiments, introduced into the reactor via the liquid inlet. As discussed above, any suitable form of water can be used, including, but not limited to, distilled water, deionized water, and the like. In some embodiments, the water is deionized water.

In some embodiments, at least a portion of the formed alcohols are removed from the reactor during the course of the reaction. The removal can be carried out in any suitable way. For example, in some embodiments, such as where an appreciable amount of the formed alcohols are present in the reactor in the vapor phase, the removal can be carried out by venting the reactor, e.g., by venting the headspace. In some embodiments, the removal occurs via a gas outlet in the reactor (described above). Further, in some embodiments, the removal can be carried out in one or more discontinuous intervals (e.g., every 15 minutes, or every 30 minutes, or every 45 minutes, etc.). Or, in some other embodiments, the addition can be carried out continuously or semi-continuously (e.g., where alcohols are being removed for at least 50% of the time during when the reaction is occurring). Any suitable amount of alcohols can be removed from the reactor during the course of the reaction. In some embodiments, at least 30% by weight, or at least 40% by weight, or at least 50% by weight, or at least 60% by weight, or at least 70% by weight, or at least 80% by weight, or at least 90% by weight, of the formed alcohols are removed from the reactor during the reaction. In some embodiments, the reaction can be run so as to achieve a certain residence time for the reactants (i.e., the dibasic ester and the water). In some embodiments, the residence time for the dibasic ester is 1 to 12 hours, or 2 to 8 hours, or 3 to 6 hours. In some embodiments, the residence time for the dibasic ester is about 4 hours. In some embodiments, the residence time for the water is 10 minutes to 12 hours, or 15 minutes to 6 hours, or 30 minutes to 3 hours. In some embodiments, the residence time for the water is about 1 hour.

In some embodiments, for example, to improve the yield, it may be desirable to ensure that the amount of formed alcohols relative to water in the reactor not rise above a certain ratio (e.g., by removal of the formed alcohols, described above). Thus, in some embodiments, the reaction is carried out such that the mole-to-mole ratio of water to formed alcohols is at least 1:1, or at least 2:1, or at least 3:1, or at least 4:1, or at least 5:1.

It was discovered that the moving of the alcohols from the reactor during the course of the reaction resulted in certain unexpected improvements over traditional hydrolysis methods. For example, the removal of the alcohols caused a dramatic reduction in reaction time, which, in turn, resulted in a product that contained far fewer impurities, such as colored impurities. There may also be fewer monobasic acid impurities in the resulting composition. In some instances, the yield was improved as well. Due to these improvements, it may be possible to reduce the amount of post-synthesis purification that must be carried out, thereby reducing the cost of making the product.

In some instances, it can be desirable to maintain a low amount of oxygen in the reactor during the reaction. Oxygen can be removed by any suitable means. For example, in some embodiments, the reactor can be purged with an inert gas or non-reactive gas (e.g., nitrogen, helium, neon, argon, methane, carbon dioxide, and the like) near the start of the reaction or even before the reaction begins. In some embodiments, the concentration of oxygen in the reactor during the reaction is kept to a concentration of no more than 500 ppm, or no more than 250 ppm, or no more than 100 ppm, or no more than 50 ppm, or no more than 10 ppm. In some embodiments, the purging gas is permanently present during the reaction.

Such reactions can often lead to the formation of colored impurities. As used herein, the term "colored impurities" refers to compounds that absorb light having a wavelength of 440 nm or 550 nm. Thus, these are compounds that absorb light in the blue-violet or the green portions of the visible electromagnetic spectrum. In some embodiments, the mole-to-mole ratio of formed dibasic acid to colored impurities is at least 250:1, or at least 350:1, or at least 500:1, or at least 1000:1, or at least 2000:1. In some embodiments, the hydrolyzed composition can be treated to lower even further the concentration of colored impurities in the composition. For example, in some such embodiments, the hydrolyzed composition can be decolorized, for example, by contacting the composition with a decolorizing agent. Suitable decolorizing agents include, but are not limited to, activated carbon, silica, silicates (e.g., magnesium silicates), clay, diatomaceous earth, and alumina. In some embodiments, for example, decolorizing agent is added to the composition, and the decolorizing agent is subsequently filtered out. Or, in some alternative embodiments, the composition can be passed through a bed containing the decolorizing agent. Additional treatments can also be carried out, either in addition to decolorization or instead of decolorization. In some embodiments, the composition can be treated with a bleaching agent (e.g., an oxidizing agent), followed by an extraction to remove the bleaching agent from the composition.

In some embodiments, the dibasic acid may be subjected to additional purification, for example, using any of the embodiments of the purification methods described below. In some other embodiments, however, such additional purification may be unnecessary.

In some embodiments, the methods described herein can lead to relatively high conversion percentages, e.g., the percentage of dibasic ester converted to dibasic acid. In some embodiments, at least 75%, or at least 80%, or at least 90%, or at least 95%, or at least 97%, or at least 99%, of the dibasic ester is converted to dibasic acid within the duration of the reaction. Further, in some embodiments, the amount of dibasic ester converted to a dibasic monoacid/monoester (e.g., a dibasic ester which reacts in such a way that, in the product, only one of the two ester groups has been converted to an acid). Thus, in some embodiments, the mole-to-mole ratio of dibasic acid to dibasic monoacid/monoester in the product is at least 25:1, or at least 35:1, or at least 50:1, or at least 100:1, or at least 200:1, or at least 300:1.

Once the dibasic acid is obtained in the desired purity, the solid can be dried. Any suitable drying technique can be used. For example, in some embodiments, the sample is dried in a drying unit, such as a rotary dryer. The dried material can be packaged in any suitable form, including, but not limited to, pellets, flakes, pastels, and the like.

FIG. 1 shows an illustrative embodiment of a method for hydrolyzing a dibasic ester to a dibasic acid. The method 100 includes: introducing a dibasic ester to a reactor 101; and reacting the dibasic ester with water in the reactor 102 to form a dibasic acid and one or more alcohols. In some embodiments, at least a portion of the formed one or more alcohols is removed from the reactor during the reacting. In some embodiments, the mole-to-mole ratio of formed dibasic acid to colored impurities is at least 250:1.

Hydrolysis Reactors

In certain aspects, the disclosure provides hydrolysis reactors, comprising: a pressurizable vessel, wherein the pressurizable vessel comprises an inlet and an outlet; a water source, wherein the water source is in fluid communication with the inlet of the pressurizable vessel; and a receiving unit, wherein the receiving unit is in fluid communication with the gas outlet of the pressurizable vessel.

The reactors include a pressurizable vessel. In some embodiments, the pressurizable reactor is a sealable vessel that can hold a pressure up to about 5 bar, or up to about 10 bar, or up to about 20 bar, or up to about 30 bar, or up to about 40 bar, or up to about 50 bar, or up to about 75 bar, or up to about 100 bar. In some embodiments, the reactor is equipped with a means of heating its contents. Thus, in some embodiments, the reactor can include one or more heating elements disposed proximate to the reaction vessel. Such heating elements can be disposed on the interior or the exterior of the reactor. Any suitable heating elements can be used, including, but not limited to, electric wires (e.g., electric heating coils), thermocouples, gas burners, heating blocks, pipes containing heated fluids (e.g., steam pipes, hot oil pipes, etc.), and the like. In some embodiments, one or more suitable heating elements can be included on the inside of the reaction vessel. In some embodiments, such internal heating elements can be the sole means used for heating the reactor contents. In other embodiments, however, such internal heating elements can be used in addition to one or more external heating elements. Because such internal heating elements may be in contact with the reactor contents, in some embodiments, the internal heating element is designed such that it can operate when in physical contact with one or more of the reactor contents. For example, in some embodiments, such internal heating elements include, but are not limited to, electric wires (e.g., electric heating coils), thermocouples, pipes containing heated fluids (e.g., steam pipes, hot oil pipes, etc.), and the like. In some other embodiments, the reactor can include a steam injection port to allow for heating by direct steam injection.

The reaction vessel can have any suitable volume and/or shape, depending on the certain factors, including, but not limited to, the nature of the reactants and products, the desired reaction temperature and pressure, the quantities of reactants. In some embodiments, the reaction vessel is a 600 mL Hastelloy C Parr reactor. In some other embodiments, the reaction vessel is a Hastelloy C pressure reactor, e.g., having a volume of 500 L to 9000 L.

In some embodiments, the reaction vessel can include various devices or structures to assist with fluid flow. Such devices or structures can include, but are not limited to, baffles, stirrers, stir bars, impellers, and the like. These elements can be disposed in the reactor in any suitable manner, depending on the desired reaction conditions, the nature of the reactor contents, and on other factors.

The reactors include an inlet and a water source, wherein the water source is in fluid communication with the inlet of the pressurizable vessel. The water source can be any suitable means for delivering water. In some embodiments, the water source is a tank. In some embodiments, the water source is a vessel suitable for holding liquid media. In some other embodiments, the water source is a tap. In some embodiments, one or more pumps can be disposed between the water source and the inlet. Any pumps suitable for pumping water can be used. The water in the water source can be any suitable form of water, including but not limited to, distilled water, deionized water, and the like. In some embodiments, the water is deionized water. In some other embodiments, the water inlet can be a steam injection port, where, for example, steam can be used to provide the reactant and to provide a hear source or a partial heat source for the reaction. In such embodiments, the port should be capable of injecting steam at a pressure of 500 to 1000 prig.

The reactors include an outlet, which is in fluid communication with a receiving unit. In some embodiments, the outlet is an outlet suitable for releasing or removing gaseous species from the reactor, e.g., during the course of a reaction. In some such embodiments, the receiving unit or vessel is a condenser, or is disposed proximate to one or more cooling elements, such that one or more of the substances contained in any gaseous stream removed from the reactor can be condensed to a liquid. In some such embodiments, one or more pressure regulators are disposed between the receiving unit and the gaseous outlet. Any suitable regulators can be used, so long as they can allow release of one or more gaseous species from the reactor without inducing a substantial reduction of reactor pressure. In some embodiments, such regulators should be capable of maintaining a pressure up to about 5 bar, or up to about 10 bar, or up to about 20 bar, or up to about 30 bar, or up to about 40 bar, or up to about 50 bar, or up to about 75 bar, or up to about 100 bar. In some embodiments, the pressure regulator is adjustable.

In some embodiments, the system could include a separator (e.g., a flash pan), which can be used, for example, to separate water in the condensed fluid from other materials in the condensed fluid (e.g., ester).

In some embodiments, the reactor may also include a gaseous inlet, such as a gaseous inlet that can be used for adding one or more gases (e.g., inert gases or non-reactive gases) to the reactor. Such an inlet can be used to sparge the reactor, e.g., during the course of the reaction. Or, in some other instances, it can be used to flush the reactor of undesired species, e.g., to flush the reactor of oxidants, such as oxygen. In some embodiments, the gas inlet is suitable for delivery of certain inert gases to the reactor, either before, during, and/or after the reaction. Such inert gases or non-reactive gases include, but are not limited to, nitrogen, helium, neon, argon, methane, carbon dioxide, and the like.

The reactor can also include various temperature and pressure detectors. Any suitable detectors can be used, depending on the environment in which it is placed and the temperature or pressure values it is intended to measure. For example, in some embodiments, the reaction vessel includes an internal temperature detector that measures the temperature in at least one location within the reactor. In some embodiments, the reaction vessel includes a pressure detector, for example, disposed in the headspace of the reactor. In some such embodiments, the pressure detector can be disposed adjacent to the gas outlet. In some embodiments, the receiving unit (e.g., condenser) can also include a temperature detector, either internal to the unit or external. In some embodiments, where a fluid line connects the gas outlet to the receiving unit, one or more temperature detectors can be disposed adjacent to said fluid line. Other temperature or pressure detectors can be disposed at various other locations in the reactor. For example, it may be desirable to include multiple temperature detectors in the reactor.

Figure 2:
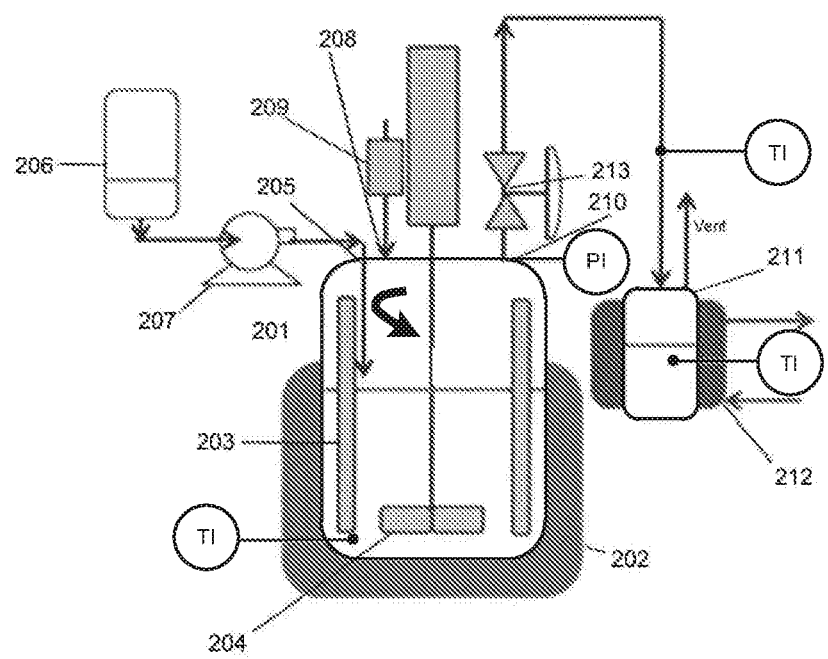
FIG. 2 shows an illustrative embodiment of a reactor suitable for hydrolyzing a dibasic ester to a dibasic acid.

FIG. 2 shows an illustrative embodiment of a reactor disclosed herein. The reactor 200 includes a reaction vessel 201, a heating block 202, baffles 203, a stirrer 204, a liquid inlet 205 in fluid communication to a water source 206 via a pump 207, an adjustable gas inlet 208 equipped with a flow meter 209, a gas outlet 210 in fluid communication with a condenser 211 having a cooling jacket 212 via an adjustable pressure regulator 213.

A reactor according to any of the aforementioned embodiments can be used to carry out the previously described methods of hydrolyzing a dibasic ester.

In some embodiments, the reaction can be run as an autocatalytic reaction wherein a portion of the dibasic acid product is seeded in the reactor (or recycled from a previous batch) to increase the reaction rate in the beginning of the reactor train. For example, in embodiments where batch reactions are carried out, the residence time may be reduced by leaving a portion of dibasic acid product in the reactor from one batch for use in the next batch. In some embodiments, multiple continuous reactors in series could be used. For example, two continuous stirred tank reactors (CSTRs) in series could be applied, where a portion of the product from the second reactor is recycled to the first reactor to maintain a high acid concentration in the first reactor. In some such embodiments, the high acid concentration would reduce the reaction time, potentially resulting in a smaller reactor size for the first reactor.

Methods of Purifying a Dibasic Acid Composition

In certain aspects, the disclosure provides methods of forming a purified solid-state dibasic acid composition, comprising: providing a first composition, which comprises a first amount of dibasic acid and a first amount of one or more monobasic acids, each dissolved in a solvent system; and cooling the first composition to form a second composition, which comprises a second amount the dibasic acid in solid-state form suspended in the solvent system, and a second amount of the one or more monobasic acids dissolved in the solvent system.

In certain embodiments, the methods include providing a first composition that includes a first amount of a dibasic acid and a first amount of one or more monobasic acids dissolved in a solvent system. As used herein, "providing" is to be given its broadest reasonable interpretation. For example, as used herein, providing can include generating a composition, but can also include receiving such a composition after it has already been generated.

Any suitable solvent system can be used, so long as at least a portion of the dibasic acid and the one or more monobasic acids are solubilized by the solvent system.

Suitable solvent systems include, but are not limited to, solvent systems comprising toluene, ortho-xylene, meta-xylene, para-xylene, acetone, dimethylformamide, tetrahydrofuran, methylene dichloride, dimethyl sulfoxide, or any mixture thereof. In some embodiments, the solvent system comprises toluene, ortho-xylene, meta-xylene, para-xylene, or any mixtures thereof. In some further embodiments, the solvent system comprises toluene. In some such embodiments, the solvent system is predominantly toluene, e.g., at least 50% by volume, or at least 70% by volume, or at least 80% by volume, or at least 90% by volume toluene.

The dibasic acid need not be entirely solubilized by the solvent system, as long as at least a portion is solubilized by the solvent system. For example, in some embodiments, at least 70%, or at least 80%, or at least 90%, or at least 95%, or at least 98% of the dibasic acid is solubilized by the solvent system.

Further, the composition can also include some amount of monobasic acid that is not solubilized by the solvent system. In such instances, the non-solubilized monobasic acid may be suitable separated from the composition by any suitable means.

In some embodiments, the initial composition is at a temperature above room temperature (e.g., above 25° C.). In some embodiments, the initial composition is at a temperature of 40° C. to 120° C., or of 50° C. to 100° C. In some embodiments, the initial composition is at a temperature not more than 20° C., or not more than 10° C., or not more than 5° C. higher than the temperature at which at least 95% of the dibasic acid is solubilized by the solvent system.

The initial composition can be disposed in any suitable vessel. In certain embodiments, the vessel is a vessel suitable for carrying out the recrystallization of organic compounds. In some embodiments, the vessel is a glass vessel, such as a glass filter reactor. In some embodiments, the vessel is also equipped with a reflux apparatus, such as a reflux condenser. In some other embodiments, the vessel can be disposed proximate to a heat source, such as a gas burner, heating block, electric wire (e.g., coil), pipes containing heated fluids, and the like. In some further embodiments, the vessel can also be equipped with an apparatus for carrying out nitrogen blanketing. In some embodiments, the vessel is equipped with a heat exchange medium that is capable of both heating and/or cooling. For example, in some embodiments, a jacketed vessel with a heat transfer fluid that is circulated and capable of being cooled by a refrigeration system and heated by electric, resistive heating.

The dibasic acid can be a dibasic acid according to any of the above embodiments. In some embodiments, the dibasic acid is a compound having the formula: H—OOC—Y—COO—H, wherein Y denotes any organic compound (such as hydrocarbyl or silyl groups), including those bearing heteroatom containing substituent groups. In some such embodiments, Y is a divalent hydrocarbyl group, which can be optionally substituted with various heteroatom-containing substituents, or whose carbon atoms can be replaced by one or more heteroatoms. Such divalent hydrocarbyl groups can include substituted and unsubstituted alkylene, alkenylene, and oxyalkylene groups.

In some embodiments, the dibasic acid is a compound of formula (II):

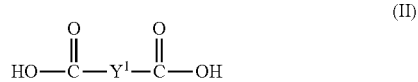

(II)

wherein, $Y^1$ is $C_{6-36}$ alkylene, $C_{6-36}$ alkenylene, $C_{6-36}$ heteroalkylene, or $C_{6-36}$ heteroalkenylene, each of which is optionally substituted one or more times by substituents selected independently from $R^3$;

$R^3$ is a halogen atom, —OH, —NH$_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some embodiments, $Y^1$ is $C_{6-36}$ alkylene, $C_{6-36}$ alkenylene, or $C_{4-36}$ oxyalkylene, each of which is optionally substituted one or more times by substituents selected from the group consisting of a halogen atom, —OH, —O($C_{1-6}$alkyl), —NH$_2$, —NH($C_{1-6}$alkyl), and N($C_{1-6}$alkyl)$_2$. In some further such embodiments, $Y^1$ is $C_{6-36}$ alkylene, $C_{6-36}$ alkenylene, or $C_{4-36}$ oxyalkylene, each of which is optionally substituted one or more times by —OH. In some further such embodiments, $Y^1$ is —(CH$_2$)$_8$—, —(CH$_2$)$_8$—, —(CH$_2$)$_{19}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{12}$—, —(CH$_2$)$_{18}$—, —(CH$_2$)$_{19}$—, —(CH$_2$)$_{20}$—, —(CH$_2$)$_{21}$—, or —(CH$_2$)$_{22}$—. In some embodiments, $Y^1$ is —(CH$_2$)$_9$—. In some embodiments, $Y^1$ is —(CH$_2$)$_{12}$—. In some embodiments, $Y^1$ is —(CH$_2$)$_{16}$—.

In some embodiments, the dibasic acid is undecanedioic acid. In some embodiments, the dibasic ester is tetradecanedioic acid. In some embodiments, the dibasic ester is octadecanedioic acid.

The methods include cooling the initial composition to form a second composition, which comprises a second amount the dibasic acid in solid-state form suspended in the solvent system, and a second amount of the one or more monobasic acids dissolved in the solvent system. The cooling can be carried out by any suitable means and at any suitable rate. In some embodiments, for example, the cooling is effected by removing the vessel from the heat source (or turning the heat source off), and allowing the composition to cool from an elevated temperature to room temperature. In some other embodiments, the composition can be cooled from a first (higher) elevated temperature and cooled to a second (lower) elevated temperature. In some such embodiments, the composition can be held at the second elevated temperature for a certain period of time, such as 5-30 minutes, or 10-20 minutes, or about 15 minutes. In some such embodiments, the first (higher) elevated temperature is 80° C. to 120° C., or 90° C. to 110° C., and the second (lower) temperature is 30° C. to 70° C., or 40° C. to 60° C. The cooling of the composition can be carried out at a rate of 0.5° C./minute to 2.0° C./minute, based on the temperature of the composition. In some embodiments, the cooling of the composition is carried out at a rate of about 1° C./minute, based on the temperature of the composition. In some other embodiments, the purification can be carried out in multiple (e.g., two) vessels specialized for recrystallization, instead of using a single vessel.

The second composition comprises an amount (i.e., a second amount) of dibasic acid in solid-state form suspended in the solvent system. As used herein, "suspended" or "suspend" or "suspension" are intended to refer broadly to any composition that includes a solid material (e.g., crystals, particles, and the like) disposed in a liquid medium. The term "suspended" does not imply that the solid material be distributed homogeneously within the liquid medium. For example, in some embodiments, the solid material may be disposed in the bottom portion of the vessel due to the force of gravity on the solid material. The suspension can be formed by any suitable means. In some embodiments, the suspension is formed by precipitating the solid material out of solution, for example, by cooling the composition, or by employing other means of inducing precipitation (e.g., altering the polarity of the solvent, and the like). In certain embodiments, at least 50%, or at least 60%, or at least 70%, or at least 80%, or at least 90%, or at least 95%, or at least 97% of the dibasic acid in the second composition is in solid-state form suspended in the solvent system (as opposed to being solubilized by the solvent system).

The second composition also includes an amount (i.e., a second amount) of the one or more monobasic acids dissolved in the solvent system. In some embodiments, at least 50%, or at least 60%, or at least 70%, or at least 80% of the monobasic acids remain dissolved in the solvent system (as opposed to precipitating out as a solid with the dibasic acid). Thus, in such embodiments, the solid material (e.g., the solid precipitate) in the second composition contains a highly pure form of the dibasic acid with a very small amount of monobasic acids. In some embodiments, monobasic acids make up less than 2 percent by weight, or less than 1.5 percent by weight, or less than 1 percent by weight, or less than 0.5 percent by weight of the solid-state material in the second composition, based on the total weight if solid-state material suspended in the solvent system in the second composition.

In some embodiments, the precipitated solid material in the second composition can be separated from the solvent system of the second composition, and washed with clean solvent. In such embodiments, the solid-state material can be further dried to yield a highly pure solid-state form of the dibasic acid.

The monobasic acids described above can include organic acids, but can also include dibasic monoesters/monoacids (e.g., that were formed due to incomplete hydrolysis of the dibasic ester to a dibasic alcohol). In some embodiments, the one or more monobasic acids are compounds of formula (IVa), compounds of formula (IVb), or any mixture thereof:

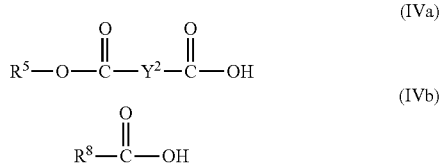

(IVa)

(IVb)

wherein:

$Y^2$ is $C_{6-36}$ alkylene, $C_{6-36}$ alkenylene, $C_{6-36}$ heteroalkylene, or $C_{6-36}$ heteroalkenylene, each of which is optionally substituted one or more times by substituents selected independently from $R^6$;

$R^5$ is $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^6$;

$R^6$ is a halogen atom, —OH, —NH$_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl;

$R^8$ is $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^9$; and $R^9$ is a halogen atom, $C_{1-6}$ alkyl, $C_{1-6}$ heteroalkyl, $C_{2-6}$ alkenyl, $C_{2-6}$ heteroalkenyl, $C_{6-14}$ aryl, $C_{2-14}$ heteroaryl, $C_{3-10}$ cycloalkyl, or $C_{2-10}$ heterocycloalkyl.

In some embodiments, $Y^2$ is $C_{6-36}$ alkylene, $C_{6-36}$ alkenylene, $C_{4-36}$ oxyalkylene, each of which is optionally substituted one or more times by substituents selected from the group consisting of a halogen atom, —OH, —O($C_{1-6}$ alkyl), —NH$_2$, —NH($C_{1-6}$ alkyl), and N($C_{1-6}$alkyl)$_2$. In some further embodiments, $Y^2$ is $C_{6-36}$ alkylene $C_{6-36}$ alkenylene, or $C_{4-36}$ oxyalkylene, each of which is optionally substituted one or more times by —OH. In some even further embodiments, $Y^2$ is —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{12}$—, —(CH$_2$)$_{18}$—, —(CH$_2$)$_{19}$—, —(CH$_2$)$_{20}$—, —(CH$_2$)$_{21}$—, or —(CH$_2$)$_{22}$—. In some embodiments, $Y^2$ is —(CH$_2$)$_9$—. In some embodiments, $Y^2$ is —(CH$_2$)$_{12}$—. In some embodiments, $Y^2$ is —(CH$_2$)$_{16}$—.

In some embodiments, $R^5$ is $C_{1-14}$ alkyl, $C_{2-14}$ alkenyl, or $C_{2-14}$ oxyalkyl, each of which is optionally substituted one or more times by —OH. In some further embodiments, $R^5$ is methyl, ethyl, propyl, isopropyl, butyl, isobutyl, sec-butyl, tert-butyl, pentyl, tert-pentyl, neopentyl, hexyl, or 2-ethylhexyl. In some even further embodiments, $R^5$ is methyl.

In some embodiments, $R^8$ is $C_{1-14}$ alkyl, $C_{2-14}$ alkenyl, or $C_{2-14}$ oxyalkyl, each of which is optionally substituted one or more times by —OH. In some further embodiments, $R^8$ is heptyl, octyl, nonyl, decyl, undecyl, dodecyl, tridecyl, tetradecyl, pentadecyl, hexadecyl, or heptadecyl. In some even further embodiments, $R^8$ is nonyl or undecyl.

Figure 3:
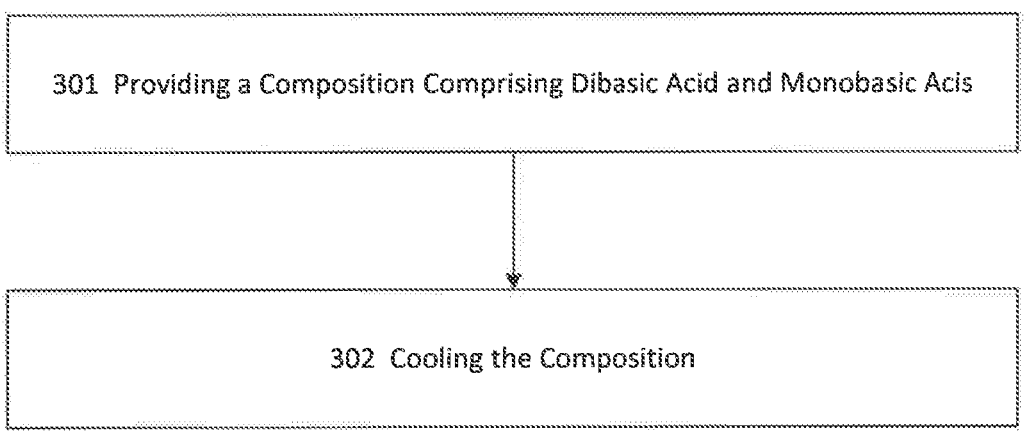
FIG. 3 shows an illustrative embodiments for forming a purified solid-state dibasic acid composition.

FIG. 3 shows an illustrative embodiments for forming a purified solid-state dibasic acid composition. The method 300 includes: providing a first composition 301, which comprises a first amount of dibasic acid and a first amount of monobasic acid, each dissolved in the solvent system; and cooling the first composition 302 to form a second composition, which comprises a second amount of the dibasic acid in solid-state form suspended in the composition, and a second amount of the one or more monobasic acids dissolved in solution.

Method of Forming a Dibasic Acid by Metathesis

In certain aspects, the disclosure provides methods of forming a dibasic acid, including: reacting a first olefin ester and an second olefin ester in the presence of a metathesis catalyst to form a first alkene and an unsaturated dibasic ester; hydrogenating the unsaturated dibasic ester to form a saturated dibasic ester; and converting the saturated dibasic ester to a saturated dibasic acid.

The methods include reacting the first olefin ester with the second olefin ester to form an unsaturated dibasic ester. Reactions of olefinic esters to make unsaturated dibasic esters are generally described in PCT Publication WO 2008/140468, and United States Patent Application Publication Nos. 2009/0264672 and 2013/0085288, all three of which are hereby incorporated by reference as though fully set forth herein in their entireties. If there is a direct or indirect contradiction between subject matter disclosed in the incorporated references and the present disclosure (e.g., definitions of the same term that differ in their scope), the description in the present disclosure controls.

As noted below, in some embodiments, one or more of the reactants for the metathesis reaction can be generated from a renewable source, e.g., by refining a natural oil or a derivative thereof. In some embodiments, the refining process includes cross-metathesizing the natural oil or a derivative thereof with an alkene. In such instances, the reactants may not be entirely pure, as certain other alkene and ester byproducts of the natural oil refining may be present in the input stream. Therefore, in some embodiments, the reactants can be subjected to a pre-treatment, such as a thermal pre-treatment, to remove certain impurities, including, but not limited to, water, volatile organics (esters and alkenes), and certain aldehydes.

Metathesis reactions can provide a useful synthetic tool for making new olefinic compounds from olefinic reactants. In general, metathesis involves an exchange of allylidene groups between two reacting olefin compounds. In some instances, the reacting compounds are the same, which can be referred to as a "self-metathesis" reaction. In other instances, however, the reacting compounds are different, which can be referred to as a "cross-metathesis reaction" reaction. Other types of metathesis reactions are also known.

Metathesis reactions can be carried out under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments were a reagent is supplied as a gas, an inert gaseous diluent can be used in the gas stream. In such embodiments, the inert atmosphere or inert gaseous diluent typically is an inert gas, meaning that the gas does not interact with the metathesis catalyst to impede catalysis to a substantial degree. For example, non-limiting examples of inert gases or non-reactive gases include helium, neon, argon, nitrogen, methane (flared), and carbon dioxide, used individually or in with each other and other inert gases or non-reacting gases.

Metathesis reactions, including those disclosed herein, can be carried out in any suitable reactor, depending on a variety of factors. Relevant factors include, but are not limited to, the scale of the reaction, the selection of conditions (e.g., temperature, pressure, etc.) the identity of the reacting species, the identity of the resulting products and the desired product(s), and the identity of the catalyst. Suitable reactors can be designed by those of skill in the art, depending on the relevant factors, and incorporated into a reaction process such, such as those disclosed herein.

The metathesis reactions disclosed herein generally occur in the presence of one or more metathesis catalysts. Such methods can employ any suitable metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in United States Patent Application Publication No. 2011/0160472, incorporated by reference herein in its entirety, except that in the event of any inconsistent disclosure or definition from the present specification, the disclosure or definition herein shall be deemed to prevail. A number of the metathesis catalysts described in United States Patent Application Publication No. 2011/0160472 are presently available from Materia, Inc. (Pasadena, Calif.).

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveyda-Grubbs-type olefin metathesis catalyst and/or an entity derived therefrom. In some embodiments, the metathesis catalyst includes a second-generation Hoveyda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) Angew. Chem. Int. Ed. Engl., 2003, 42, 4592-4633; (b) Chem. Rev., 2002, 102, 145-179; and/or (c) Chem. Rev., 2009, 109, 3211-3226, each of which is incorporated by reference herein in its entirety, except that in the event of any inconsistent disclosure or definition from the present specification, the disclosure or definition herein shall be deemed to prevail.

In certain embodiments, the metathesis catalyst is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil or unsaturated ester (e.g., as an auger feed).

The metathesis reaction temperature may, in some instances, be a rate-controlling variable where the temperature is selected to provide a desired product at an acceptable rate. In certain embodiments, the metathesis reaction temperature is greater than −40° C., or greater than −20° C., or greater than 0° C., or greater than 10° C. In certain embodiments, the metathesis reaction temperature is less than 200° C., or less than 150° C., or less than 120° C. In some embodiments, the metathesis reaction temperature is between 0° C. and 150° C., or is between 10° C. and 120° C.

The metathesis reaction can be run under any desired pressure. In some instances, it may be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than 0.1 atm (10 kPa), or greater than 0.3 atm (30 kPa), or greater than 1 atm (100 kPa). In some embodiments, the reaction pressure is no more than about 70 atm (7000 kPa), or no more than about 30 atm (3000 kPa). In some embodiments, the pressure for the metathesis reaction ranges from about 1 atm (100 kPa) to about 30 atm (3000 kPa).

In some embodiments, the first olefin ester and the second olefin ester are both terminal olefin esters, meaning that they have a terminal carbon-carbon double bond. In some such embodiments, the terminal olefin esters are independently compounds of formula (V):

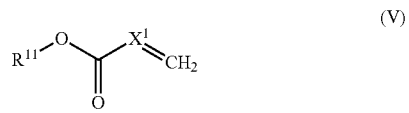 (V)

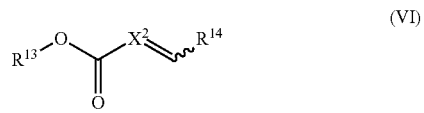 (VI)

wherein:

$X^1$ is $C_{3-18}$ alkylene, $C_{3-18}$ alkenylene, $C_{2-18}$ heteroalkylene, or $C_{2-18}$ heteroalkenylene, each of which is optionally substituted one or more times by substituents selected independently from $R^{12}$;

$R^{11}$ is $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^{12}$; and $R^{12}$ is a halogen atom, —OH, —$NH_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some such embodiments, $X^1$ is $C_{3-18}$ alkylene, $C_{3-18}$ alkenylene, or $C_{2-18}$ oxyalkylene, each of which is optionally substituted one or more times by substituents selected from the group consisting of a halogen atom, —OH, —O($C_{1-6}$ alkyl), —$NH_2$, —NH($C_{1-6}$ alkyl), and N($C_{1-6}$ alkyl)$_2$. In some further embodiments, $X^1$ is $C_{3-18}$ alkylene, $C_{3-18}$ alkenylene, or $C_{2-18}$ oxyalkylene, each of which is optionally substituted one or more times by —OH. In some even further embodiments, $X^1$ is —$(CH_2)_2$—CH=, —$(CH_2)_3$—CH=, —$(CH_2)_4$—CH=, —$(CH_2)_5$—CH=, —$(CH_2)_6$—CH=, —$(CH_2)_7$—CH=, —$(CH_2)_8$—CH=, —$(CH_2)_9$—CH=, —$(CH_2)_{10}$—CH=, —$(CH_2)_{11}$—CH=, —$(CH_2)_{12}$—CH=, —$(CH_2)_{13}$—CH=, —$(CH_2)_{14}$—CH=, or —$(CH_2)_{15}$—CH=. In some even further embodiments, $X^1$ is —$(CH_2)_7$—CH=.

In some such embodiments, $R^{11}$ is $C_{1-8}$ alkyl, $C_{2-8}$ alkenyl, or $C_{1-8}$ oxyalkyl, each of which is optionally substituted one or more times by —OH. In some further embodiments, $R^{11}$ is methyl, ethyl, propyl, isopropyl, butyl, isobutyl, sec-butyl, tert-butyl, pentyl, tert-pentyl, neopentyl, hexyl, or 2-ethylhexyl. In some even further embodiments, $R^{11}$ is methyl.

In some embodiments, the terminal olefin esters are different compounds. In some other embodiments, however, the terminal olefin esters are the same compound. In some embodiments, the terminal olefins esters are both esters of 9-decenoic acid, for example, in some further embodiments, both terminal olefin esters are 9-decenoic acid methyl ester.

When the terminal olefins esters react, an olefinic byproduct (e.g., an alkene) is also produced. In some embodiments, where the terminal olefin esters react to form an unsaturated dibasic ester, the resulting alkene is ethylene. The formed ethylene can be vented from the reactor during the course of the reaction, or can be allowed to stay in the reactor. Metathesis reactions that generate the desired unsaturated dibasic esters can be referred to as "productive metathesis," as the catalyst is used to make the desired product. In some instances, however, two terminal olefin esters can react in a way that simply regenerates two new molecules of the same terminal olefin esters that served as reactants. Such metathesis reactions can be referred to as "unproductive metathesis," as the catalyst is used to make products besides the desired unsaturated dibasic esters.

In some other embodiments, the first olefin ester and the second olefin ester are both internal olefin esters. In some such embodiments, the first olefin ester and the second olefin ester are independently compounds of formula (VI):

wherein:

$X^2$ is $C_{3-18}$ alkylene, $C_{3-18}$ alkenylene, $C_{248}$ heteroalkylene, or $C_{248}$ heteroalkenylene, each of which is optionally substituted one or more times by substituents selected independently from $R^{15}$;

$R^{13}$ is $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^{15}$;

$R^{14}$ is $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^{15}$; and $R^{15}$ is a halogen atom, —OH, —$NH_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some such embodiments, $X^2$ is $C_{3-18}$ alkylene, $C_{3-18}$ alkenylene, or $C_{2-18}$ oxyalkylene, each of which is optionally substituted one or more times by substituents selected from the group consisting of a halogen atom, —OH, —O($C_{1-6}$ alkyl), —$NH_2$, —NH($C_{1-6}$ alkyl), and N($C_{1-6}$ alkyl)$_2$. In some further such embodiments, $X^2$ is $C_{3-18}$ alkylene, $C_{3-18}$ alkenylene, or $C_{2-18}$ oxyalkylene, each of which is optionally substituted one or more times by —OH. In some even further such embodiments, $X^2$ is —$(CH_2)_2$—CH=, —$(CH_2)_3$—CH=, —$(CH_2)_4$—CH=, —$(CH_2)_5$—CH=, —$(CH_2)_6$—CH=, —$(CH_2)_7$—CH=, —$(CH_2)_8$—CH=, —$(CH_2)_9$—CH=, —$(CH_2)_{10}$—CH=, —$(CH_2)_{11}$—CH=, —$(CH_2)_{12}$—CH=, —$(CH_2)_{13}$—CH=, —$(CH_2)_{14}$—CH=, or —$(CH_2)_{15}$—CH=. In some such embodiments, $X^2$ is —$(CH_2)_7$—CH=.

In some such embodiments, $R^{13}$ is $C_{1-8}$ alkyl, $C_{2-8}$ alkenyl, or $C_{1-8}$ oxyalkyl, each of which is optionally substituted one or more times by —OH. In some further such embodiments, $R^{13}$ is methyl, ethyl, propyl, isopropyl, butyl, isobutyl, sec-butyl, tert-butyl, pentyl, tert-pentyl, neopentyl, hexyl, or 2-ethylhexyl. In some even further such embodiments, RB is methyl.

In some such embodiments, $R^{14}$ is $C_{1-8}$ alkyl, $C_{2-8}$ alkenyl, or $C_{1-8}$ oxyalkyl, each of which is optionally substituted one or more times by —OH. In some further such embodiments, $R^{14}$ is methyl, ethyl, propyl, butyl, pentyl, hexyl, heptyl, octyl, or nonyl. In some even further such embodiments, $R^{14}$ is methyl or ethyl. In some embodiments, $R^{14}$ is ethyl.

In some embodiments, the internal olefin esters are different compounds. In some other embodiments, however, the internal olefin esters are the same compound. In some embodiments, the internal olefins esters are both esters of 9-dodecenoic acid, for example, in some further embodiments, both internal olefin esters are 9-dodecenoic acid methyl ester. In some other embodiments, the internal olefins esters are both esters of 9-undecenoic acid, for example, in some further embodiments, both internal olefin esters are 9-undecenoic acid methyl ester.

When the internal olefin esters react, an olefinic byproduct (e.g., an alkene) is also produced. In some embodiments, where the internal olefin esters react to form an unsaturated dibasic ester, the resulting alkene is an internal alkene. The identity of the formed internal alkenes will vary depending on the identity of the reacting internal olefin esters. In some embodiments, the resulting internal olefin ester is 2-butene, 2-pentene, 2-hexene, 3-hexene, 3-heptene, 4-octene, and the like. In some embodiments, the resulting internal olefin is 2-butene. In some other embodiments, the resulting internal olefin is 3-hexene. The formed internal alkene can be vented from the reactor during the course of the reaction, or can be allowed to stay in the reactor. As noted above, metathesis reactions that generate the desired unsaturated dibasic esters can be referred to as "productive metathesis," as the catalyst is used to make the desired product. In some instances, however, two internal olefin esters can react in a way that simply generates two new internal olefin esters. Such metathesis reactions can be referred to as "unproductive metathesis," as the catalyst is used to make products besides the desired unsaturated dibasic esters.

In some other embodiments, the first olefin ester is a terminal olefin ester and the second olefin is an internal olefin ester. In some such embodiments, the terminal olefin ester is a compound of formula (V), as disclosed above, including all further embodiments thereof. In some such embodiments, the internal olefin ester is a compound of formula (VI), as disclosed above, including all further embodiments thereof. In some such embodiments, the terminal olefin ester is an ester of 9-decenoid acid, such as 9-decenoic acid methyl ester. In some such embodiments, the internal olefin ester is an ester of 9-undecenoic acid or an ester of 9-dodecenoic acid, such as 9-undecenoic acid methyl ester or 9-dodecenoic acid methyl ester, respectively.

When the terminal olefin ester reacts with the internal olefin ester, an olefinic byproduct (e.g., an alkene) is also produced. In some embodiments, where the terminal olefin ester and the internal olefin ester react to form an unsaturated dibasic ester, the resulting alkene is a terminal alkene. The identity of the formed internal alkenes will vary depending on the identity of the reacting internal olefin ester. In some embodiments, the resulting terminal olefin ester is propene, 1-butene, 1-pentene, 1-hexene, and the like. In some embodiments, the resulting internal olefin is propene. In some other embodiments, the resulting internal olefin is 1-butene. The formed terminal alkene can be vented from the reactor during the course of the reaction, or can be allowed to stay in the reactor. As noted above, metathesis reactions that generate the desired unsaturated dibasic esters can be referred to as "productive metathesis," as the catalyst is used to make the desired product. In some instances, however, terminal and internal olefin esters can react in a way that simply generates a terminal olefin ester and an internal olefin ester. Such metathesis reactions can be referred to as "unproductive metathesis," as the catalyst is used to make products besides the desired unsaturated dibasic esters.

The embodiments above describe different ways in which metathesis reactions can be used to make an unsaturated dibasic ester. In some instances, however, two or more different productive metathesis reactions may be occurring at the same time. For example, in embodiments where the first olefin ester is a terminal olefin ester and the second olefin ester is an internal olefin ester, the terminal olefin ester and the internal olefin ester may each react with other molecules of the same compound, such that two self-metathesis reactions may compete with the cross-metathesis reaction. Also, in some embodiments, the terminal olefin ester can be generated from the internal olefin ester, e.g., by reacting the internal olefin ester with a terminal alkene in the presence of a metathesis catalyst. Or, in some alternative embodiments, the internal olefin ester can be generated from the terminal olefin ester, e.g., by reacting the terminal olefin ester with an internal alkene in the presence of a metathesis catalyst. In instances where the cross-metathesis reaction of the terminal olefin ester and the internal olefin ester can be kinetically favored, and where only a single olefin ester may be available, it can be advantageous to use such processes to generate different olefin esters, so as to allow for cross-metathesis to occur at the expense of self-metathesis.

The method includes hydrogenating the unsaturated dibasic ester to generate a saturated dibasic ester. The hydrogenation can be carried by any suitable means. In certain embodiments, hydrogen gas is reacted with the unsaturated dibasic ester in the presence of a hydrogenation catalyst to form a saturated dibasic acid, for example, in a hydrogenation reactor.

Any suitable hydrogenation catalyst can be used. In some embodiments, the hydrogenation catalyst comprises nickel, copper, palladium, platinum, molybdenum, iron, ruthenium, osmium, rhodium, or iridium, individually or in any combinations thereof. Such catalysts may be heterogeneous or homogeneous. In some embodiments, the catalysts are supported nickel or sponge nickel type catalysts. In some embodiments, the hydrogenation catalyst comprises nickel that has been chemically reduced with hydrogen to an active state (i.e., reduced nickel) provided on a support. The support may comprise porous silica (e.g., kieselguhr, infusorial, diatomaceous, or siliceous earth) or alumina. The catalysts are characterized by a high nickel surface area per gram of nickel. Commercial examples of supported nickel hydrogenation catalysts include those available under the trade designations NYSOFACT, NYSOSEL, and NI 5248 D (from BASF Catalysts LLC, Iselin, N.J.). Additional supported nickel hydrogenation catalysts include those commercially available under the trade designations PRICAT Ni 62/15 P, PRICAT Ni 55/5, PPRICAT 9910, PRICAT 9920, PRICAT 9908, PRICAT 9936 (from Johnson Matthey Catalysts, Ward Hill, Mass.).

The supported nickel catalysts may be of the type described in U.S. Pat. Nos. 3,351,566, 6,846,772, European Patent Publication No. 0168091, and European Patent Publication No. 0167201, each of which are incorporated by reference herein in their entireties. Hydrogenation may be carried out in a batch or in a continuous process and may be partial hydrogenation or complete hydrogenation. In certain embodiments, the temperature ranges from about 50° C. to about 350° C., about 100° C. to about 300° C., about 150° C. to about 250° C., or about 100° C. to about 150° C. The desired temperature may vary, for example, with hydrogen gas pressure. Typically, a higher gas pressure will require a lower temperature. Hydrogen gas is pumped into the reaction vessel to achieve a desired pressure of $H_2$ gas. In certain embodiments, the $H_2$ gas pressure ranges from about 15 psig (1 barg) to about 3000 psig (204.1 barg), about 15 psig (1 barg) to about 90 psig (6.1 barg), or about 100 psig (6.8 barg) to about 500 psig (34 barg). As the gas pressure increases, more specialized high-pressure processing equipment may be required. In certain embodiments, the reaction conditions are "mild," wherein the temperature is approximately between approximately 50° C. and approximately 100° C. and the $H_2$ gas pressure is less than approximately 100 psig. In other embodiments, the temperature is between about 100° C. and about 150° C., and the pressure is between about 100 psig (6.8 barg) and about 500 psig (34 barg). When the desired degree of hydrogenation is reached, the reaction mass is cooled to the desired filtration temperature.

The amount of hydrogenation catalyst is typically selected in view of a number of factors including, for example, the type of hydrogenation catalyst used, the amount of hydrogenation catalyst used, the degree of unsaturation in the material to be hydrogenated, the desired rate of hydrogenation, the desired degree of hydrogenation (e.g., as measure by iodine value (IV)), the purity of the reagent, and the H$_2$ gas pressure. In some embodiments, the hydrogenation catalyst is used in an amount of about 10 percent by weight or less, for example, about 5 percent by weight or less or about 1 percent by weight or less.

Following the metathesis (described above) the resulting composition can contain various impurities. These impurities can be compounds that were made by various kinds of unproductive metathesis. Or, in some instances, the impurities may result from the presence of impurities in the starting compositions. In any event, it can, in some embodiments, be desirable to strip out and/or distill out these impurities. In some such embodiments, the stripping and/or distilling can occur after the metathesis, but before the hydrogenation. In some alternative embodiments, the stripping and/or distilling can occur after both the metathesis and the hydrogenation. These impurities may contain more esters than hydrocarbons (e.g., monobasic esters), as certain alkene impurities can be vented out of the reactor during the metathesis reaction, e.g., due to the lower relative boiling point of the alkene impurities. Of course, in some instances, these alkene impurities may stay in the reactor long enough to involve themselves in certain metathesis reactions, thereby generating other impurities (e.g., an additional alkene impurity and an additional ester impurity). Paraffin impurities can also be present, which can be removed by the stripping and/or distilling, for example, after hydrogenation.

In some embodiments, the stripping may lead to the removal of certain amounts of the first olefin ester and/or the second olefin ester. In some such embodiments, these stripped out reactants can be collected and reused for further metathesis reactions.

In some embodiments, it may be desirable to further purify the saturated dibasic ester prior to the converting. For example, in some embodiments, the saturated dibasic ester can be recrystallized. The recrystallization can be carried out by any suitable technique. In general, the dissolved in a solvent system, for example, with heating, followed by cooling until solid crystals of the saturated dibasic ester appear. This can be a suitable means of removing impurities that are more soluble in the solvent system than the saturated dibasic ester, e.g., shorter-chain monobasic and dibasic esters and/or acids.

The method includes converting the saturated dibasic ester to a saturated dibasic acid. The concerting can be carried out by any suitable means. In some embodiments, the saturated dibasic ester is hydrolyzed according to any of the embodiments described above. In some other embodiments, the saturated dibasic ester is converted to a saturated dibasic acid by saponification, followed by acidification.

The resulting saturated dibasic acid can be a dibasic acid according to any of the above embodiments. In some embodiments, the dibasic acid is a compound having the formula: H—OOC—Y—COO—H, wherein Y denotes any organic compound (such as hydrocarbyl or silyl groups), including those bearing heteroatom containing substituent groups. In some such embodiments, Y is a divalent hydrocarbyl group, which can be optionally substituted with various heteroatom-containing substituents, or whose carbon atoms can be replaced by one or more heteroatoms. Such divalent hydrocarbyl groups can include substituted and unsubstituted alkylene, alkenylene, and oxyalkylene groups.

In some embodiments, the dibasic acid is a compound of formula (II):

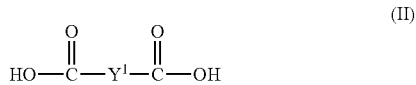

(II)

wherein, $Y^1$ is $C_{6-36}$alkylene or $C_{6-36}$ heteroalkylene, each of which is optionally substituted one or more times by substituents selected independently from $R^3$; and $R^3$ is a halogen atom, —OH, —NH$_2$, $C_{1-6}$alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some embodiments, $Y^1$ is $C_{6-36}$alkylene or $C_{4-36}$ oxyalkylene, each of which is optionally substituted one or more times by substituents selected from the group consisting of a halogen atom, —OH, —O($C_{1-6}$alkyl), —NH$_2$, —NH($C_{1-6}$alkyl), and N($C_{1-6}$alkyl)$_2$. In some further such embodiments, $Y^1$ is $C_{6-36}$alkylene, $C_{6-36}$alkenylene, or $C_{4-36}$ oxyalkylene, each of which is optionally substituted one or more times by —OH. In some further such embodiments, $Y^1$ is —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{17}$—, —(CH$_2$)$_{18}$—, —(CH$_2$)$_{19}$—, —(CH$_2$)$_{20}$—, —(CH$_2$)$_{21}$—, or —(CH$_2$)$_{22}$—. In some embodiments, $Y^1$ is —(CH$_2$)$_9$—. In some embodiments, $Y^1$ is —(CH$_2$)$_{12}$—. In some embodiments, $Y^1$ is —(CH$_2$)$_{16}$—.

In some embodiments, the saturated dibasic acid is undecanedioic acid. In some embodiments, the dibasic ester is tetradecanedioic acid. In some embodiments, the dibasic ester is octadecanedioic acid.

In some embodiments, the saturated dibasic acid can be further purified. In some embodiments, the purification is carried out using the recrystallization methods described above.

Figure 4:
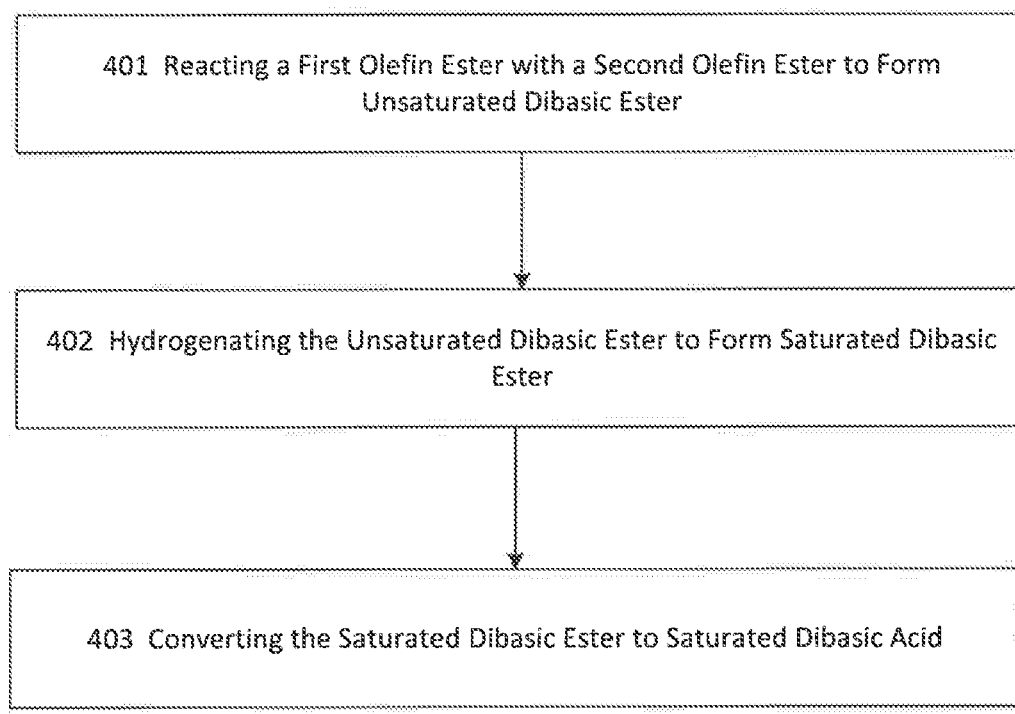
FIG. 4 shows an illustrative embodiment for forming a dibasic acid.

FIG. 4 shows an illustrative embodiment for forming a dibasic acid. The method 400 includes: reacting a first olefin ester with a second olefin ester 401 in the presence of a metathesis catalyst to form a first alkene and an unsaturated dibasic ester; hydrogenating the unsaturated dibasic ester 402 to form a saturated dibasic ester; and converting the saturated dibasic ester 403 to form a saturated dibasic acid.

Figure 5:
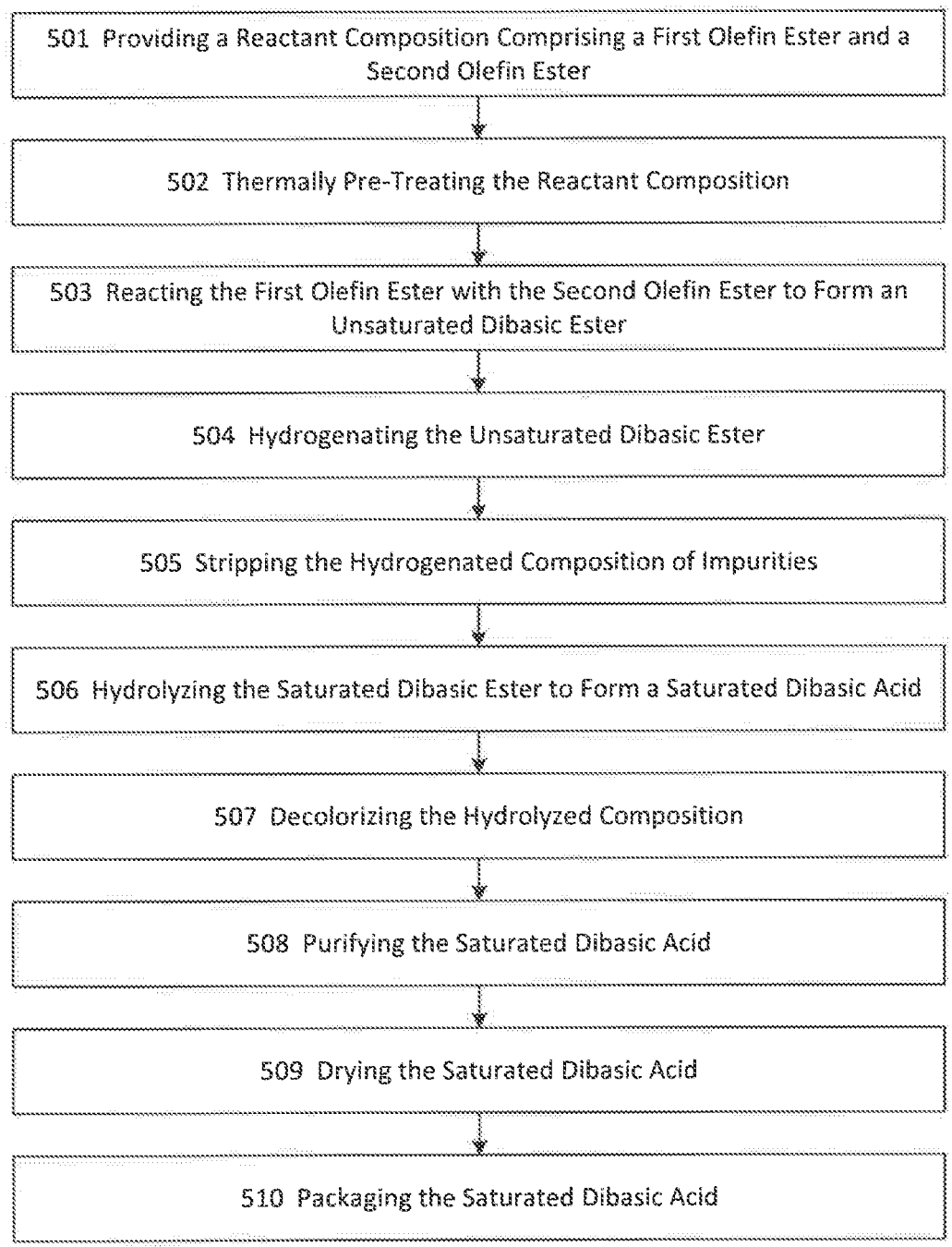
FIG. 5 shows an illustrative embodiment for forming a dibasic acid.

FIG. 5 shows an illustrative embodiment for forming a dibasic acid. The method 500 includes: providing a reactant composition comprising a first olefin ester and a second olefin ester 501; thermally pre-treating the reactant composition 502; reacting the first olefin ester with the second olefin ester 503 in the presence of a metathesis catalyst to form an unsaturated dibasic acid; hydrogenating the unsaturated dibasic ester 504 to form a saturated dibasic ester (including optional recovery of the hydrogenation catalyst, e.g., by filtration); stripping the hydrogenated composition 505 of certain alkene and ester impurities; reacting the saturated dibasic acid with water 506 to form a saturated dibasic acid; decolorizing the hydrolyzed composition 507 (including recovery of the decolorizing agent); purifying the saturated dibasic acid (e.g., by recrystallization) 508; drying the solid saturated dibasic acid 509; and packaging of the saturated dibasic acid 510. In some embodiments, the saturated dibasic acid is octadecanedioic acid. In some such embodiments, the first and second olefin esters are 9-decenoic acid methyl ester. In some other such embodiments, the first and the second olefin esters are both 9-dodecenoic acid methyl ester. In some even further such embodiments, the first olefin ester is 9-decenoic acid methyl ester and the second olefin ester is 9-decenoid acid methyl ester.

Figure 6:
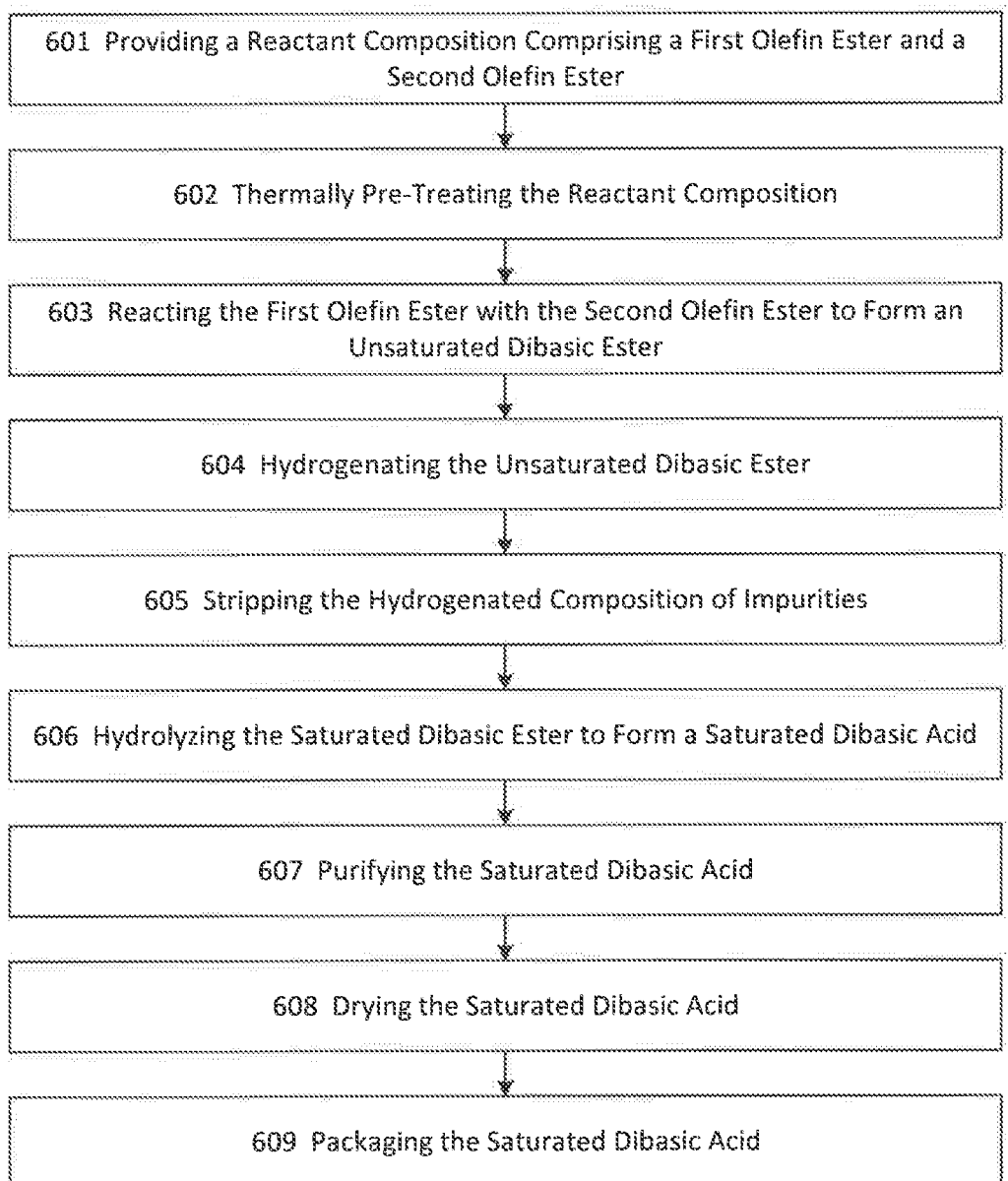
FIG. 6 shows an illustrative embodiment for forming a dibasic acid.

FIG. 6 shows an illustrative embodiment for forming a dibasic acid. The method 600 includes: providing a reactant composition comprising a first olefin ester and a second olefin ester 601; thermally pre-treating the reactant composition 602; reacting the first olefin ester with the second olefin ester 603 in the presence of a metathesis catalyst to form an unsaturated dibasic acid; hydrogenating the unsaturated dibasic ester 604 to form a saturated dibasic ester (including optional recovery of the hydrogenation catalyst, e.g., by filtration); stripping the hydrogenated composition 605 of certain alkene and ester impurities; reacting the saturated dibasic acid with water 606 to form a saturated dibasic acid; purifying the saturated dibasic acid (e.g., by recrystallization) 607; drying the solid saturated dibasic acid 608; and packaging of the saturated dibasic acid 609. In some embodiments, the saturated dibasic acid is octadecanedioic acid. In some such embodiments, the first and second olefin esters are 9-decenoic acid methyl ester. In some other such embodiments, the first and the second olefin esters are both 9-dodecenoic acid methyl ester. In some even further such embodiments, the first olefin ester is 9-decenoic acid methyl ester and the second olefin ester is 9-decenoid acid methyl ester.

Figure 7:
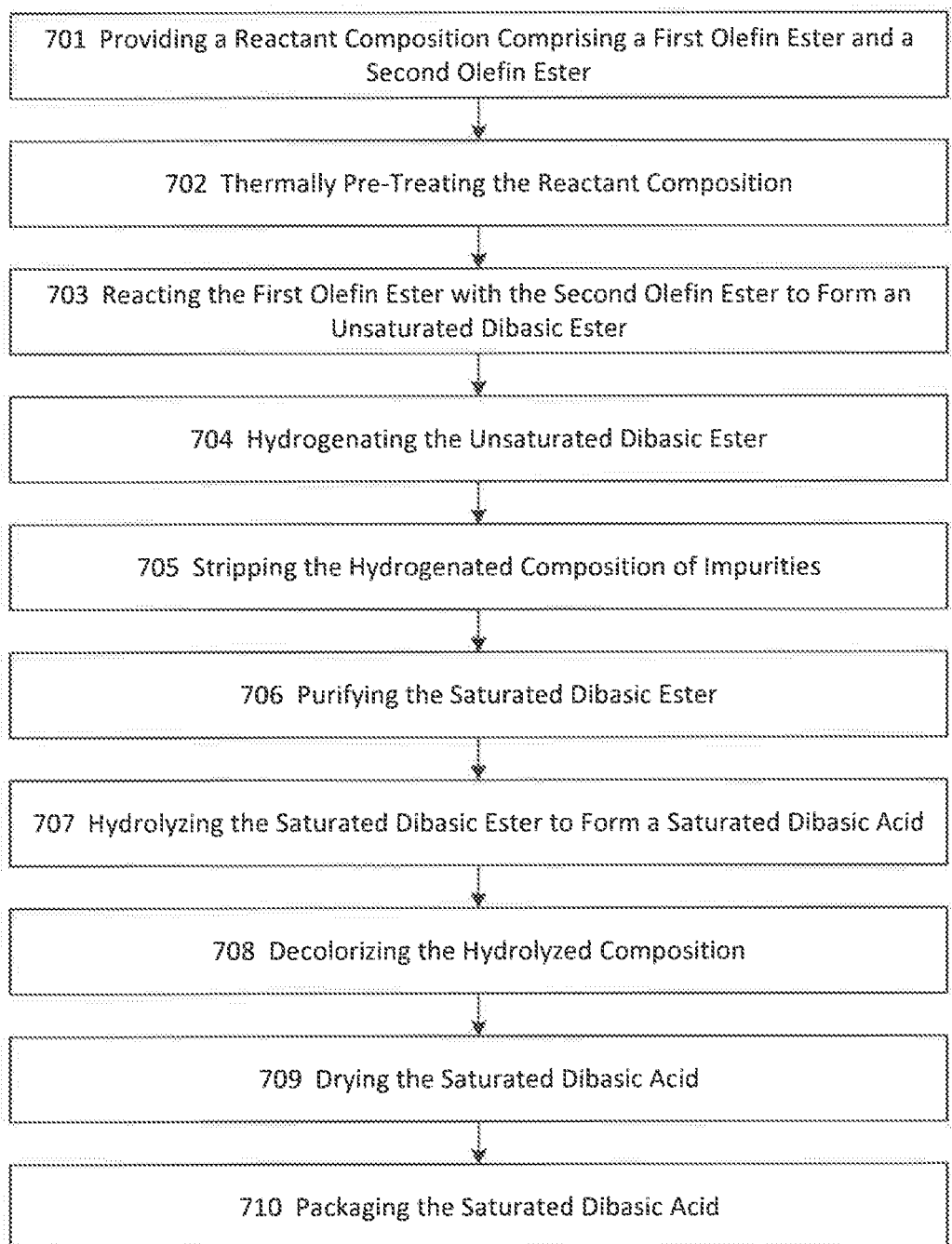
FIG. 7 shows an illustrative embodiment for forming a dibasic acid.

FIG. 7 shows an illustrative embodiment for forming a dibasic acid. The method 700 includes: providing a reactant composition comprising a first olefin ester and a second olefin ester 701; thermally pre-treating the reactant composition 702; reacting the first olefin ester with the second olefin ester 703 in the presence of a metathesis catalyst to form an unsaturated dibasic acid; hydrogenating the unsaturated dibasic ester 704 to form a saturated dibasic ester (including optional recovery of the hydrogenation catalyst, e.g., by filtration); stripping the hydrogenated composition 705 of certain alkene and ester impurities; purifying the saturated dibasic ester, e.g., by recrystallization 706; reacting the saturated dibasic acid with water 707 to form a saturated dibasic acid; decolorizing the hydrolyzed composition 708 (including recovery of the decolorizing agent); drying the solid saturated dibasic acid 709; and packaging of the saturated dibasic acid 710. In some embodiments, the saturated dibasic acid is octadecanedioic acid. In some such embodiments, the first and second olefin esters are 9-decenoic acid methyl ester. In some other such embodiments, the first and the second olefin esters are both 9-dodecenoic acid methyl ester. In some even further such embodiments, the first olefin ester is 9-decenoic acid methyl ester and the second olefin ester is 9-decenoid acid methyl ester.

Figure 8:
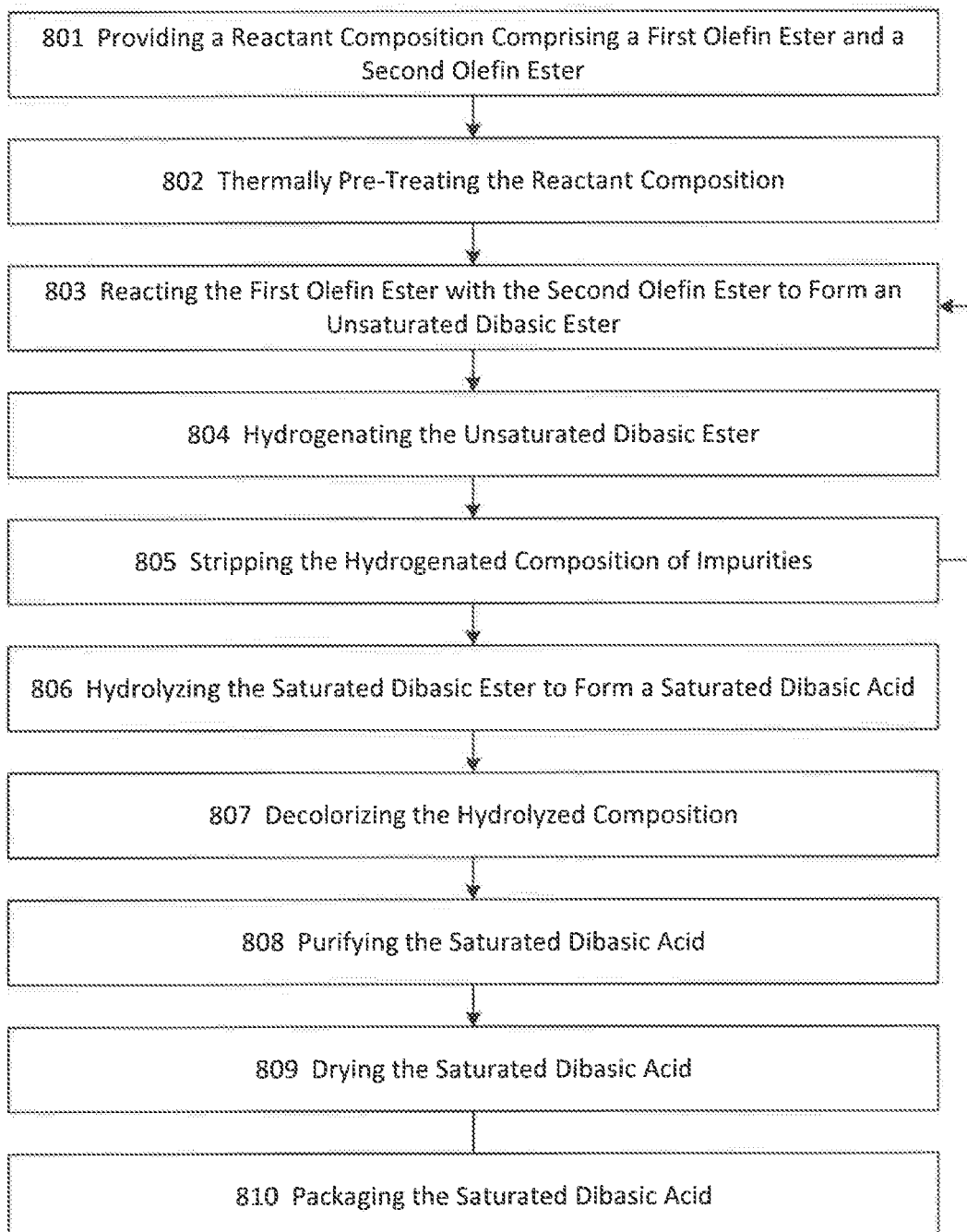
FIG. 8 shows an illustrative embodiment for forming a dibasic acid.

FIG. 8 shows an illustrative embodiment for forming a dibasic acid. The method 800 includes: providing a reactant composition comprising a first olefin ester and a second olefin ester 801; thermally pre-treating the reactant composition 802; reacting the first olefin ester with the second olefin ester 803 in the presence of a metathesis catalyst to form an unsaturated dibasic acid; hydrogenating the unsaturated dibasic ester 804 to form a saturated dibasic ester (including optional recovery of the hydrogenation catalyst, e.g., by filtration); stripping the hydrogenated composition 805 of certain alkene and ester impurities, wherein the stripped impurities include amounts of the first olefin ester and the second olefin ester, which are collected and reused in subsequent metathesis reactions 803; reacting the saturated dibasic acid with water 806 to form a saturated dibasic acid; decolorizing the hydrolyzed composition 807 (including recovery of the decolorizing agent); purifying the saturated dibasic acid (e.g., by recrystallization) 808; drying the solid saturated dibasic acid 809; and packaging of the saturated dibasic acid 810. In some embodiments, the saturated dibasic acid is octadecanedioic acid. In some such embodiments, the first and second olefin esters are 9-decenoic acid methyl ester. In some other such embodiments, the first and the second olefin esters are both 9-dodecenoic acid methyl ester. In some even further such embodiments, the first olefin ester is 9-decenoic acid methyl ester and the second olefin ester is 9-decenoid acid methyl ester.

Derivation from Renewable Sources:

The dibasic esters, internal olefin esters, and/or terminal olefins employed in any of the above aspects and embodiments can, in certain embodiments, be derived from renewable sources, such as various natural oils. Any suitable methods can be used to make these compounds from such renewable sources. Suitable methods include, but are not limited to, fermentation, conversion by bioorganisms, and conversion by metathesis.

Olefin metathesis provides one possible means to convert certain natural oil feedstocks into olefins and esters that can be used in a variety of applications, or that can be further modified chemically and used in a variety of applications. In some embodiments, a composition (or components of a composition) may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical properties.

A wide range of natural oils, or derivatives thereof, can be used in such metathesis reactions. Examples of suitable natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Metathesized natural oils can also be used. Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Such natural oils, or derivatives thereof, can contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain olefins, e.g., ethylene, propylene, or 1-butene, and where the natural oil includes esters of oleic acid, an amount of 1-decene, among other products, is formed. Following transesterification, for example, with an alkyl alcohol, an amount of 9-denenoic acid methyl ester is formed. In some such embodiments, a separation step may occur between the metathesis and the transesterification, where the alkenes are separated from the esters. In some other embodiments, transesterification can occur before metathesis, and the metathesis is performed on the transesterified product.

In some embodiments, the natural oil can be subjected to various pre-treatment processes, which can facilitate their utility for use in certain metathesis reactions. Useful pre-treatment methods are described in United States Patent Application Publication No. 2011/0113679 and U.S. Provisional Patent Application Nos. 61/783,321 and 61/783,720, both filed Mar. 14, 2013, all three of which are hereby incorporated by reference as though fully set forth herein.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, terminal olefins and internal olefins may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, the methods disclosed herein can employ multiple metathesis reactions. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The conditions for such metathesis reactions, and the reactor design, and suitable catalysts are as described above with reference to the metathesis of the olefin esters. That discussion is incorporated by reference as though fully set forth herein.

In the embodiments above, the natural oil (e.g., as a glyceride) is metathesized, followed by transesterification. In some other embodiments, transesterification can precede metathesis, such that the fatty acid esters subjected to metathesis are fatty acid esters of monohydric alcohols, such as methanol, ethanol, or isopropanol.

Figure 9:
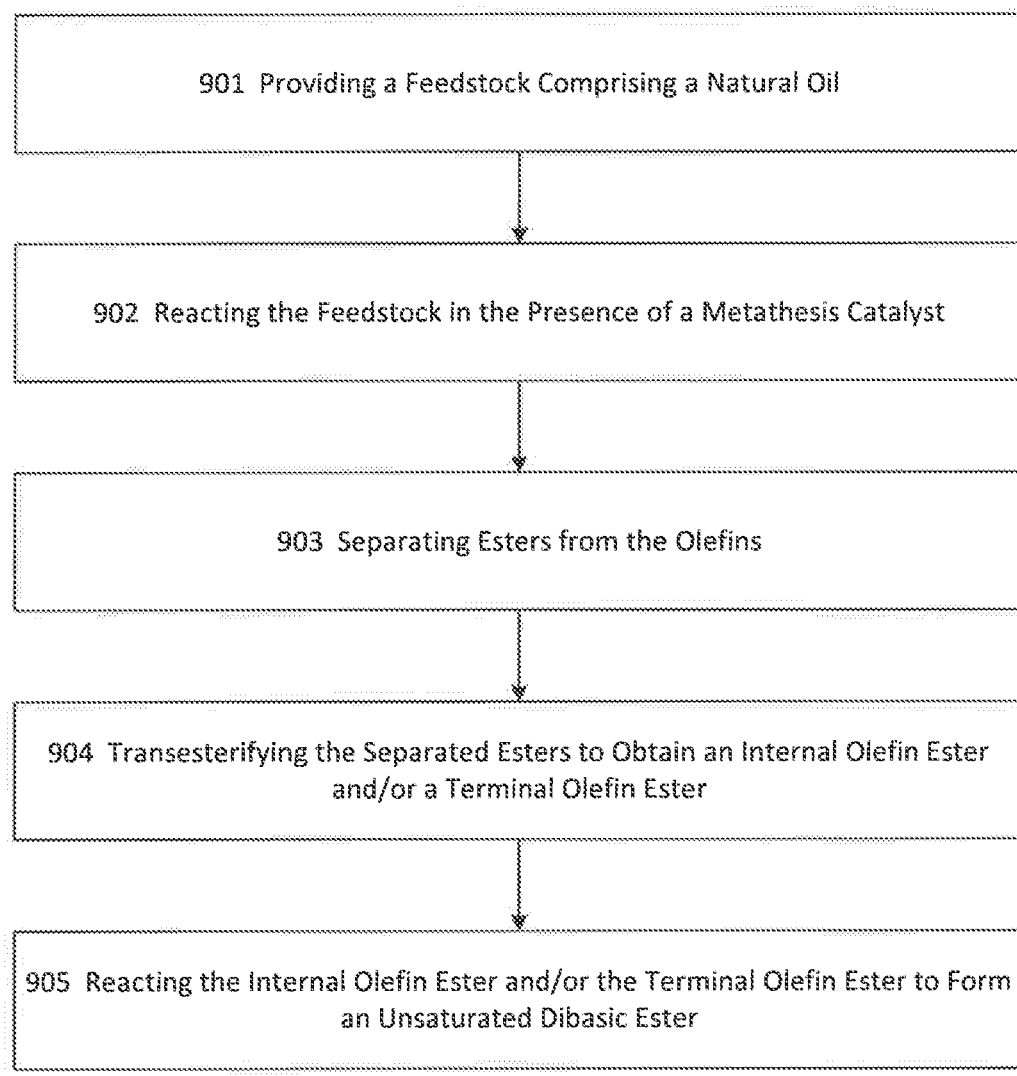
FIG. 9 shows an illustrative embodiment for making an unsaturated dibasic ester from a feedstock comprising a natural oil.

FIG. 9 shows a flow chart that illustrates certain embodiments for making an unsaturated dibasic ester from a feedstock comprising a natural oil. The illustrated method 900 comprises: providing a feedstock comprising a natural oil 901; reacting the feedstock in the presence of a metathesis catalyst 902 to form a metathesized product that comprises esters, e.g., unsaturated glycerides, and olefins; separating (at least a portion of) the esters from the olefins 903 in the metathesized product; transesterifying the separated esters 904, e.g., in the presence of an alcohol (e.g., methanol) to form a terminal olefin ester and/or an internal olefin ester; and reacting the internal olefin ester and/or the terminal olefin ester (according to any of the aspects and embodiments described above) 905 to form an unsaturated dibasic ester. The unsaturated dibasic ester can, for example, be further reacted according to any of the above aspects and embodiments to form a saturated dibasic acid, such as octadecanedioic acid.

Figure 10:
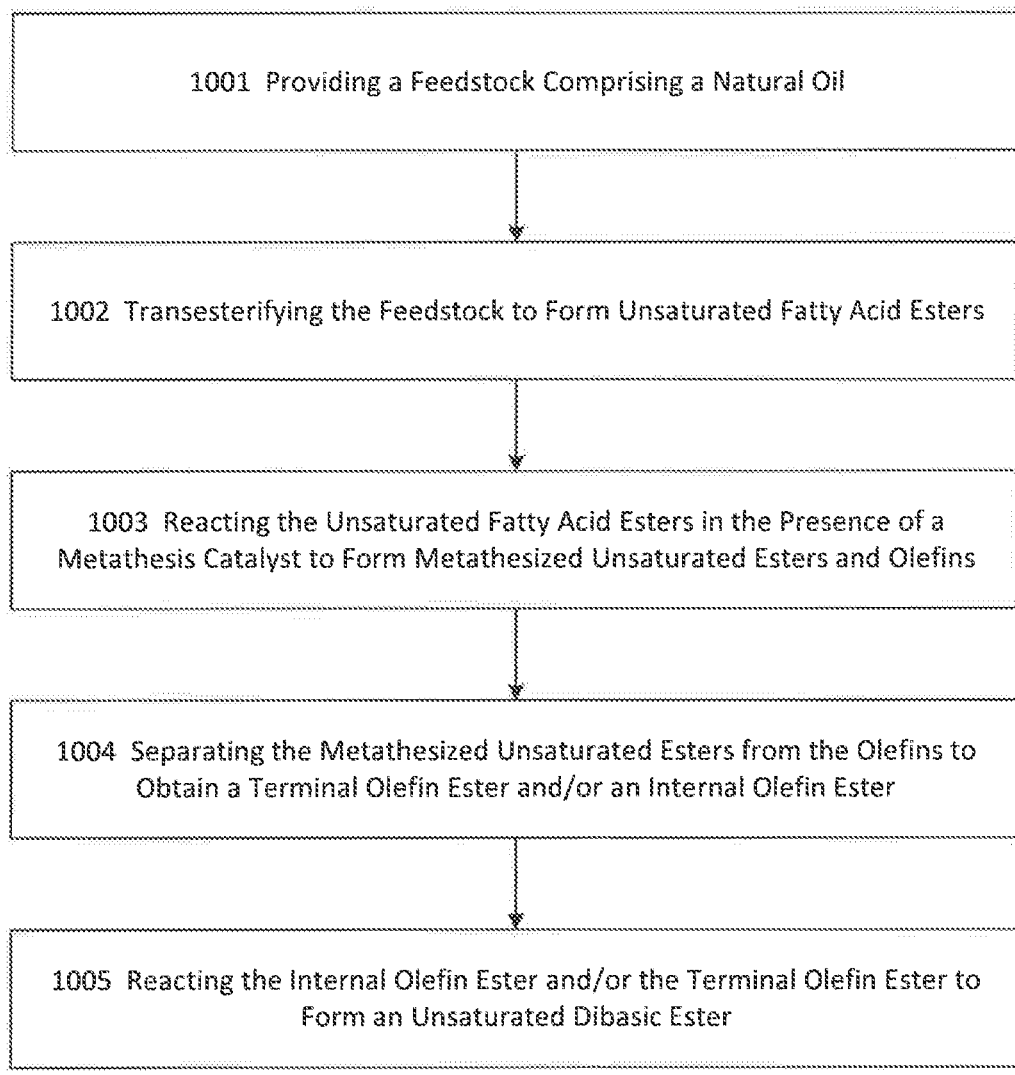
FIG. 10 shows an illustrative embodiment for making an unsaturated dibasic ester from a feedstock comprising a natural oil.

FIG. 10 shows a flow chart that illustrates certain embodiments for making an unsaturated dibasic ester from a feedstock comprising a natural oil. The illustrated method 1000 comprises: providing a feedstock comprising a natural oil 1001; transesterifying the feedstock 1002, e.g., in the presence of an alcohol (e.g., methanol) to form a transesterified product comprising one or more unsaturated fatty acid esters; reacting the unsaturated fatty acid esters 1003, e.g., in the presence of a metathesis catalyst to form a metathesized product comprising one or more metathesized unsaturated esters and one or more olefins; separating (at least a portion of) the metathesized unsaturated esters from the olefins 1004, e.g., in the metathesized product, wherein the separated metathesized product comprises a terminal olefin ester and/or an internal olefin ester; and reacting the internal olefin ester and/or the terminal olefin ester (according to any of the aspects and embodiments described above) 1005 to form an unsaturated dibasic ester. The unsaturated dibasic ester can, for example, be further reacted according to any of the above aspects and embodiments to form a saturated dibasic acid, such as octadecanedioic acid.

EXAMPLES

Examples 1A & 1B—Direct Hydrolysis of 1,18-Octadecanedioic Acid Dimethyl Ester (ODDAME)

A 203.4 gram sample of solid ODDAME was charged into a 600 mL Hastelloy C Parr reactor vessel equipped with a baffle and two sets of 4×45° pitch blade impellers, internal thermocouple, and sampling dip tube. The ODDAME sample was recrystallized prior to being charged into the vessel. Then, 106.9 grams of deionized water was charged into the reactor. The reactor vessel was sealed and disposed into the reactor, illustrated in FIG. 2. The reactor included an aluminum block heater, an overhead stir motor, and a vent line equipped with a pressure regulator that connects to a condenser. The reactor also has a water feed system.

The reaction mixture was heated to 100° C. to melt the ODDAME (m.p. ~60° C.) under a continuous nitrogen purge (900 sccm) in the reactor headspace. The pressure regulator on the reactor vent line was adjusted until the pressure in the reactor was measured as ~360 prig. After the regulator was set, the reactor vessel was leak tested at targeted reactor pressure, and the headspace of the system was purged with nitrogen for 30 minutes at 900 sccm. The system was then heated to 225° C. (internal reactor temperature) at 1000 rpm stir rate under a nitrogen purge headspace of 900 sccm. The condensate receiver was cooled to <15° C. using a glycol chiller system. When the internal reactor reached 223° C., the time was referenced as 0 minutes (e.g., start of the timed reaction). As the reaction proceeded, condensate was retrieved from the condenser (i.e., condensate receiver) every 30 minutes, and the mass of the condensate was measured. Over the ensuing 30 minutes, following the collection of the condensate, water was charged into the reaction vessel at the time-averaged mass rate of the condensate collected in the condenser during the previous 30-minute interval (i.e., mass of condensate collected in previous 30 minute interval/30 minutes). For Example 1A, the reaction proceeded for 6 hours at ~225° C. For Example 1B, the reaction proceeded for 8 hours at ~225° C. Then, the water feed was stopped and the reactor pressure was decreased gradually to remove water from the reactor. After most of the water was removed from the reactor, the reactor contents were transferred under a nitrogen atmosphere to a glass container. Nitrogen headspace maintained until reactor contents reach at room temperature. The masses of the water and the reactor contents were measured.

A portion of the sample was analyzed by gas chromatograph (GC). About 1 gram of the wet sample was dissolved in toluene (~10 grams) at 95-100° C. Then, 500 µL of the top layer was transferred to a 2 mL GC vial. Then 400 µL of N,O-bis(trimethylsilyl)trifluoroacetamide (Aldrich Chemical Co., St. Louis, Mo., USA) was added to the GC vial. The vial was sealed and then heated at 60° C. for 2 hours under agitation (230 rpm shaking) until the mixture became homogeneous. Then, the silylated material was diluted with 300 µL of ethyl acetate. The vial sample was analyzed on a GC equipped with an FID detector, a hydrogen carrier gas, and a Restek TG65 capillary column.

Results are reported in Table 1. As used herein, the "Conversion %" is a molar percent and is: $100*\{[2X_{ODDAME}+X_{ODDA(H)ME}]_{initial}-[2X_{ODDAME}+X_{ODDA(H)ME}]_{final}\}/[2X_{ODDAME}+X_{ODDA(H)ME}]_{initial}$, where ODDAME refers to 1,18-octadecanedioic acid dimethyl ester, ODDA(H)ME refers to 1,18-octadecanedioic acid monomethyl ester, and $X_{ODDAME}$ and $X_{ODDA(H)ME}$ refer to the mole fraction of ODDAME and ODDA(H)ME, respectively. As used herein, "ODDA Yield %" is a molar percent and is: $100*X_{ODDA}/[X_{ODDA}+X_{ODDAME}+X_{ODDA(H)ME}]$, where $X_{ODDA}$ is the mole fraction of ODDA, and the other terms have the meanings as defined above. As used herein, "ODDA(H)ME Yield %" is a molar percent and is: $100*X_{ODDA(H)ME}/[X_{ODDA}+X_{ODDAME}+X_{ODDA(H)ME}]$, where the terms have the meanings as defined above. As used herein, the "Overall Water:Oil Molar Ratio" is Z*[(mass of water initially)+(mass of water added during reaction)/(mass of water initially), where Z is 10 for a 10:1 initial water-to-oil molar ratio, and is 40 for a 40:1 initial water-to-oil molar ratio.

TABLE 1

|  | Example 1A | Example 1B |
| --- | --- | --- |
| Overall Hydrolysis Reaction Time (hours) | 6 | 8 |
| Initial Water-to-Oil Molar Ratio | 10 | 10 |
| Overall Water:Oil Molar Ratio | 42.5 | 80.4 |
| ODDA(H)Me (%, molar) | 4.9 | 0.40 |
| Conversion (%, molar) | 97.3 | 99.8 |

Example 1C—Direct Hydrolysis of ODDAME

A 185.0 gram sample of solid ODDAME was charged into a 600 mL Hastelloy C Parr reactor vessel equipped with a baffle and two sets of 4×45° pitch blade impellers, internal thermocouple, and sampling dip tube. Then, 97.2 grams of deionized water was charged into the reactor. The reactor vessel was sealed and disposed into the reactor, illustrated in FIG. 2. The reactor included an aluminum block heater, an overhead stir motor, and a vent line equipped with a pressure regulator that connects to a condenser. The reactor also has a water feed system.

The reaction mixture was heated to 100° C. to melt the ODDAME (m.p. ~60° C.) under a continuous nitrogen purge (500 sccm) in the reactor headspace. The pressure regulator on the reactor vent line was adjusted until the pressure in the reactor was measured as ~360 prig. After the regulator was set, the reactor vessel was leak tested at targeted reactor pressure, and the headspace of the system was purged with nitrogen for 30 minutes at 900 sccm. The system was then heated to 225° C. (internal reactor temperature) at 1000 rpm stir rate under a nitrogen purge headspace of 500 sccm. The condensate receiver was cooled to <15° C. using a glycol chiller system. When the internal reactor reached 223° C., the time was referenced as 0 minutes (e.g., start of the timed reaction). As the reaction proceeded, condensate was retrieved from the condenser (i.e., condensate receiver) every 30 minutes, and the mass of the condensate was measured. Over the ensuing 30 minutes, following the collection of the condensate, water was charged into the reaction vessel at the time-averaged mass rate of the condensate collected in the condenser during the previous 30-minute interval (i.e., mass of condensate collected in previous 30 minute interval/30 minutes). The reaction proceeded for 6 hours at ~225° C. Then, the water feed was stopped and the reactor pressure was decreased gradually to remove water from the reactor. After most of the water was removed from the reactor, the reactor contents were transferred under a nitrogen atmosphere to a glass container. Nitrogen headspace maintained until reactor contents reach at room temperature. The masses of the water and the reactor contents were measured.

A portion of the sample was analyzed by gas chromatograph (GC). About 1 gram of the wet sample was dissolved in toluene (~10 grams) at 95-100° C. Then, 500 µL of the top layer was transferred to a 2 mL GC vial. Then 400 µL of N,O-bis(trimethylsilyl)trifluoroacetamide (Aldrich Chemical Co., St. Louis, Mo., USA) was added to the GC vial. The vial was sealed and then heated at 60° C. for 2 hours under agitation (230 rpm shaking) until the mixture became homogeneous. Then, the silylated material was diluted with 300 µL of ethyl acetate. The vial sample was analyzed on a GC equipped with an FID detector, a hydrogen carrier gas, and a Restek TG65 capillary column. Results are reported in Table 2.

TABLE 2

|  | Example 1C |
| --- | --- |
| Overall Hydrolysis Reaction Time (hours) | 6 |
| Initial Water-to-Oil Molar Ratio | 10 |
| Overall Water:Oil Molar Ratio | 30.7 |
| ODDA(H)Me (%, molar) | 3.4 |
| Conversion (%, molar) | 98.3 |

Example 1D—Direct Hydrolysis of ODDAME

A 203.4 gram sample of solid ODDAME was charged into a 600 mL Hastelloy C Parr reactor vessel equipped with a baffle and two sets of 4×45° pitch blade impellers, internal thermocouple, and sampling dip tube. The ODDAME sample was recrystallized prior to being charged into the vessel. Then, 106.9 grams of deionized water was charged into the reactor. The reactor vessel was sealed and disposed into the reactor, illustrated in FIG. 2. The reactor included an aluminum block heater, an overhead stir motor, and a vent line equipped with a back-pressure regulator that connects to a condenser. The reactor also has a water feed system.

The reaction mixture was heated to 75° C. to melt the ODDAME (m.p. ~60° C.) under a nitrogen in the reactor headspace. Once a temperature of 75° C. was reached, the reactor vessel was leak tested at targeted reactor pressure, and the headspace of the system was purged with nitrogen for 30 minutes at 900 sccm. The system was then heated to 225° C. (internal reactor temperature) at 1000 rpm stir rate under a nitrogen purge headspace of 900 sccm. The condensate receiver was cooled to <15° C. using a glycol chiller system. When the internal reactor reached 223° C., The time was referenced as 0 minutes (e.g., start of the timed reaction). The ~500 sccm headspace nitrogen was sweep through the reactor vent line and the vent was adjusted until the pressure in the reactor was measured as ~300 prig at time zero to remove 135 grams/hour condensate. As the reaction proceeded, condensate was retrieved from the condenser (i.e., condensate receiver) every 15 minutes, and the mass of the condensate was measured. Over the ensuing 15 minutes, following the collection of the condensate, water was charged into the reaction vessel at the time-averaged mass rate of the condensate collected in the condenser during the previous 15-minute interval (i.e., mass of condensate collected in previous 15 minute interval/15 minutes). The reaction proceeded for 4 hours at ~225° C. Then, the water feed was stopped and the reactor pressure was decreased gradually to remove water from the reactor purge with 250 sccm nitrogen headspace. After most of the water was removed from the reactor, the reactor contents were transferred under a nitrogen atmosphere to a glass container. Nitrogen headspace maintained until reactor contents reach at room temperature. The masses of the water and the reactor contents were measured. The sample was dried.

About 40 mg of the dry sample was placed into a 2 mL GC vial and add 0.40 mL of N,O-bis(trimethylsilyl)trifluoroacetamide (Aldrich Chemical Co., St. Louis, Mo., USA). The vial was sealed and then heated at 60° C. for 2 hours under agitation (230 rpm shaking) until the mixture became homogeneous. Then, the silylated material was diluted with 300 µL of ethyl acetate. The vial sample was analyzed on a GC equipped with an FID detector, a hydrogen carrier gas, and a Restek TG65 capillary column. Results are reported in Table 3.

TABLE 3

|  | Example 1D |
| --- | --- |
| Overall Hydrolysis Reaction Time (hours) | 4 |
| Initial Water-to-Oil Molar Ratio | 10 |
| Overall Water:Oil Molar Ratio | 59.6 |
| ODDA(H)Me (%, molar) | 2.9 |
| Conversion (%, molar) | 98.2 |

Comparative Examples 1A & 1B—Direct Hydrolysis of ODDAME

For Comparative Examples 1A and 1B, 90.0 kg sample of solid ODDAME and 190 kg of deionized water were charged to a 500 L Hastelloy C pressure reactor (R-0371), equipped with a hot oil jacket. For 1068-69-2, 8.4 kg of solid ODDA (CG400C-121101, from ODDA recovered from 1068-69-1) was also charged into the reactor. The reactor lid was secured, and the agitation was started at 100 rpm. The reactor was inerted with nitrogen by pressurizing the reactor with nitrogen to 0.3 MPa, followed by venting to atmospheric pressure for a total of four pressure-vent cycles.

Cycle A:

The reactor temperature was increased to 225° C. over the course of 5 to 6 hours. The reactor temperature was held at 225° C. for 4 hours. After 4 hours at 225° C., the jacket temperature was cooled 150° C. over the course of 2 to 3 hours. At 150° C., the reactor pressure was decreased to atmospheric pressure and held at atmospheric pressure and 150° C. for 5 to 6 hours to evaporate the water and methanol generated from the reaction. The vessel was then recharged with 190 kg of deionized water. Cycle A was repeated an additional 5 times over 5 days. After completion of distillation of methanol and water of the final cycle, the inner temp was adjusted between 90 and 100° C. Then, 270 kg of toluene was charged to the reactor and the temperature setpoint was adjusted between 90 and 95° C. An azeotropic mixture of toluene and water was distilled away from the ODDA in the 500 L reactor at atmospheric pressure. The distillation was stopped when the batch temperature increased from 85 to 95° C. Then, 90 kg of azeotropic mixture was removed from the reactor during the distillation.

Then, another 70 kg of toluene was then recharged to the reactor and the reactor was reheated to between 90 and 95° C. The ODDA and toluene were transferred under nitrogen into a 500-L mobile tank, which was preheated to a jacket temperature between 90 and 95° C. A 1000-L glass-lined reactor (R-0322) was preheated to a jacket temperature between 90 and 95° C. The ODDA-toluene solution from the 500-L mobile tank was transferred under nitrogen into the reactor 1000-L glass-lined vessel, and the agitation in the 1000-L vessel was started at 80 rpm. An additional 170 kg toluene was charged into the 500 L Hastelloy C reactor (R-0371). The reactor was reheated to between 90 and 95° C. The toluene was transferred under nitrogen into the 500-L mobile tank, which was preheated to a jacket temperature between 90 and 95° C. The toluene solution from the 500-L mobile tank was then transferred under nitrogen into the reactor 1000-L glass-lined vessel containing the toluene and ODDA solution. Then, 6.6 kg of charcoal (GA) was added to the 1000-L glass-lined vessel containing the ODDA and toluene. The temperature of the vessel was reheated to between 90 and 95° C. and held between 90 and 95° C. for 2 hours under 80 rpm stirring. After 2 hours, the batch was filtered through a Celite bed into a 1000-L stainless steel vessel (R-0321). The filter was preheated with a steam jacket, and the Celite was preheated by a hot toluene flush, prior to transfer of the batch.

The mixture in the 1000-L stainless steel vessel (R-0321) was slowly cooled to 20±5° C. over the course of 5 to 6 hours under agitation (80 rpm). The mixture was then pressure filtered, routing the filtrate to the 1000-L glass-lined reactor. The filter cake was centrifuged to remove free solvent and to generate a wet cake. The wet cake was vacuumed dried (ca. −0.086 MPa) in double-cone oven at between 60 and 65° C. for 24 hours. The product was collected in polypropylene bags, and the weight and the purity were analyzed. The results of the analysis are shown in Table 4. The results from Examples 1A-1C indicate the potential to achieve similar conversion and purity using one-third the overall hydrolysis reaction time while consuming about one-third the amount of water relative to a batch-cycle reaction mode.

TABLE 4

|  | Comparative Example 1A | Comparative Example 1B |
| --- | --- | --- |
| Overall Hydrolysis Reaction Time (hours) | 24 | 24 |
| Initial Water-to-Oil Molar Ratio | 40 | 40 |
| Overall Water:Oil Molar Ratio | 240 | 240 |
| ODDA(H)Me (%, molar) | 0.06 | 0.65 |
| Conversion (%, molar) | 99.8 | 99.2 |

Example 2—Comparison of Color in Samples

Samples prepared according to Examples 1A-1D and Comparative Examples 1A and 1B were analyzed for the presence of colored impurities. For each sample, 1 g of the ODDA sample was added to 3 g of dimethylsulfoxide (DMSO). The sample was heated to 60° C. until dissolved. The sample was transferred to a clear 1-cm-wide cuvette and analyzed for percent transmittance (% T) of light at wavelengths of 440 nm and 550 nm, respectively. A reference of DMSO was used. The results for each sample are listed below in Table 5.

TABLE 5

|  | % T at 440 nm | % T at 550 nm |
|---|---|---|
| Example 1A | 93.7 | 96.2 |
| Example 1B | 98.7 | 99.7 |
| Example 1C | 96.7 | 98.0 |
| Example 1D | 93.3 | 94.1 |
| Comparative Example 1A | 66.8 | 84.2 |
| Comparative Example 1B | 45.8 | 69.1 |

The percent transmittances of ODDA samples generated according to Examples 1A-1C are higher than the percent transmittances of ODDA generated from Comparative Examples 1A and 1B. Therefore, the method of Examples 1A-1C may obviate the need for additional purification, or may reduce the amount of additional purification required.

Example 3A—Purification of ODDA

A 150-mL glass filter reactor was charged with 10 g ODDA prepared according to Example 1A and 100 mL toluene (Aldrich, 99.8%, anhydrous). The reactor was equipped with a reflux condenser, a thermocouple, and a nitrogen blanket. The contents were mechanically stirred using an overhead agitator, and the reactor jacket was heated to 104° C. The solids were dissolved, and the measured internal temperature (solution) was 95° C. The jacket was then cooled at a rate to afford an internal temperature decrease of about 1° C./minute. Solids appeared at 75.6° C. Cooling was continued at a rate of about 1° C./minute to achieve an internal temperature of about 50° C. The solution was held at about 50° C. for 15 minutes, and the solids were filtered using a 10-micron filter with a slight nitrogen pressure. The solids were then washed with 25 mL of fresh toluene and dried under a nitrogen flow for about 2 hours. The solids were then removed from the vessel and dried overnight at 80° C.

The dried samples were weighed and the mass was recorded. A portion of the sample was derivatized using N,O-bis(trimethylsilyl)trifluoroacetamide (BTSFA, Aldrich) and analyzed by gas chromatography (gas chromatograph equipped with a FID, hydrogen carrier gas, and a Restek TG65 capillary column). Composition results are reported using area and area percent of the chromatogram. Table 6 describes the composition of the sample before purification and after purification. Table 6 recites the weight percent of ODDA in each sample, the weight percent of dibasic acids (diacids) in each sample, and the weight percent of monobasic acids (monoacids) in each sample.

TABLE 6

|  | Pre-Purification Sample (wt %) | Post-Purification Sample (wt %) |
|---|---|---|
| ODDA Purity | 94.6 | 98.6 |
| Total Diacid Purity | 95.4 | 99.2 |
| Total Monoacid Impurity | 4.4 | 0.8 |

Example 3B—Purification of ODDA

A 150-mL glass filter reactor was charged with 10 g ODDA prepared according to Example 1C and 100 mL toluene (Aldrich, 99.8%, anhydrous). The reactor was equipped with a reflux condenser, a thermocouple, and a nitrogen blanket. The contents were mechanically stirred using an overhead agitator, and the reactor jacket was heated to 97° C. The solids were dissolved, and the measured internal temperature (solution) was 95.0° C. The jacket was then cooled at a rate of about 1° C./minute (internal solution temperature). Solids appeared at 71.7° C. (internal solution temperature). Cooling was continued at a rate of about 1° C./minute to achieve an internal temperature of about 50° C. The solution was held at about 50° C. for 15 minutes, and the solids were filtered using a 10-micron filter with a slight nitrogen pressure. The solids were then washed with 25 mL of fresh toluene and dried under a nitrogen flow for about 2 hours. About 1 g of solids were removed from the vessel and dried overnight at 80° C.

The remaining solids were suspended in 100 mL of fresh toluene (Aldrich, anhydrous, 99.8%) in the 150-mL filter reactor. The ODDA was redissolved in toluene at about 95° C. The jacket was then cooled at a rate of about 1° C./minute (internal solution temperature). Solids appeared at 75.5° C. (solution). Cooling was continued at a rate of about 1° C./minute to achieve an internal temperature of about 50° C. The solution was held at about 50° C. for 15 minutes and the solids were filtered using a 10-micron filter with a slight nitrogen pressure. The solids were then washed with 25 mL of fresh toluene and dried under nitrogen flow for about 2 hours. The solids were removed from the vessel and dried overnight at 80° C.

The dried samples were weighed and mass was recorded. A portion of the sample was derivatized using N,O-bis(trimethylsilyl)trifluoroacetamide (BTSFA, Aldrich) and analyzed by gas chromatography (gas chromatograph equipped with a FID, hydrogen carrier gas, and a Restek TG65 capillary column). Composition results are reported using area and area percent of the chromatogram. Table 7 describes the composition of the sample before purification and after purification. Table 7 recites the weight percent of ODDA in each sample, the weight percent of dibasic acids (diacids) in each sample, and the weight percent of monobasic acids (monoacids) in each sample.

TABLE 7

|  | Before Sample Purification (wt %) | After First Purification (wt %) | After Second Purification (wt %) |
|---|---|---|---|
| ODDA Purity | 93.1 | 96.0 | 98.4 |
| Total Diacid Purity | 94.0 | 99.0 | 99.8 |
| Total Monoacid Impurity | 6.0 | 1.0 | 0.2 |

What is claimed is:

1. A method of hydrolyzing a dibasic ester, comprising:
introducing a first composition to a reactor, the first composition comprising at least 50 grams of a dibasic ester of formula (I) and an initial amount of water:

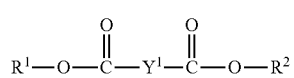

(I)

wherein
Y$^1$ is —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —$(CH_2)_{17}$—, —$(CH_2)1_8$—, —$(CH_2 19_8$—, —$(CH_2)_{20}$—, —$(CH_2)_{21}$—, or —$(CH_2)_{22}$—; and
$R^1$ and $R^2$ are independently $C_{1-8}$ alkyl, $C_{2-8}$ alkenvl, or $C_{2-8}$ oxyalkenyl, each of which is optionally substituted one or more times by —OH; and reacting the dibasic ester in the reactor with water to form a second composition comprising a dibasic acid and alcohols, wherein the dibasic acid is a compound of formula (II) and the alcohols are compounds of formula (111a) and formula (111b):

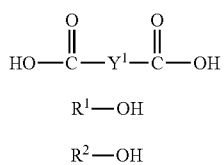

wherein $Y^1$, $R^1$ and $R^2$ are as defined above for formula (I);

wherein during the reacting, at least a portion of the alcohols is removed from the reactor and additional amounts of water are added to the reactor, and wherein the mass-to-mass ratio of the additional amounts of water added during the reaction to the alcohols removed during the reaction ranges from 0.8:1 to 1.2:1.

2. The method of claim 1, wherein the yield of dibasic acid is at least 75 percent.

3. The method of claim 1, wherein $R^1$ and $R^2$ are independently methyl, ethyl, propyl, isopropyl, butyl, isobutyl, sec-butyl, tert-butyl, pentyl, tert-pentyl, neopentyl, hexyl, or 2-ethylhexyl.

4. The method of claim 3, wherein $R^1$ and $R^2$ are methyl.

5. The method of claim 1, wherein the reacting is carried out at a reactor temperature of 40° C. to 300° C.

6. The method of claim 1, wherein at least 20 percent by weight of the alcohols are removed from the reactor during the reacting.

7. The method of claim 1, wherein the alcohols are removed continuously or semi-continuously during the reacting.

8. The method of claim 1, wherein the water is added continuously or semi-continuously during the reacting.

9. The method of claim 1, wherein the mole-to-mole ratio of water to alcohols in the reactor is at least 1:1 during the reacting.

10. The method of claim 9, wherein the mole-to-mole ratio of water to alcohols in the reactor is at least 2:1 during the reacting.

11. The method of claim 1, wherein the concentration of $O_2$ in the reactor does not exceed 250 ppm during the reacting, based on the total number of gaseous species in the reactor.

12. A method of hydrolyzing a dibasic ester, comprising:
introducing a first composition to a reactor, the first composition comprising at least 50 grams of a dibasic ester of formula (I):

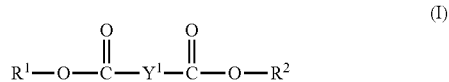

wherein
$Y^1$ is —$(CH_2)_{13}$—, —$(CH_2)_{14}$—, —$(CH_2)_{15}$—, —$(CH_2)_{16}$—, —$(CH_2)_{17}$—, —$(CH_2)1_8$—, —$(CH_2 19_8$—, —$(CH_2)_{20}$—, —$(CH_2)_{21}$—, or —$(CH_2)_{22}$—; and
$R^1$ and $R^2$ are independently $C_{1-8}$ alkyl, $C_{2-8}$ alkenvl, or $C_{2-8}$ oxyalkenyl, each of which is optionally substituted one or more times by —OH; and reacting the dibasic ester in the reactor with water to form a second composition comprising a dibasic acid and alcohols, wherein the dibasic acid is a compound of formula (II) and the alcohols are compounds of formula (111a) and formula (111b):

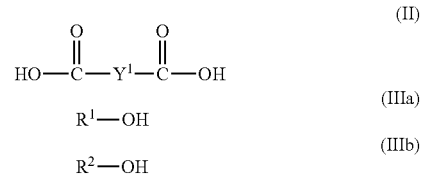

wherein $Y^1$, $R^1$ and $R^2$ are as defined above for formula (I);

wherein during the reacting, at least a portion of the alcohols is removed from the reactor and water is added to the reactor, and wherein the mass-to-mass ratio of the water added during the reaction to the alcohols removed during the reaction ranges from 0.8:1 to 1.2:1.

13. The method of claim 12, wherein the yield of dibasic acid is at least 75 percent.

14. The method of claim 12, wherein $R^1$ and $R^2$ are independently methyl, ethyl, propyl, isopropyl, butyl, isobutyl, sec-butyl, tert-butyl, pentyl, tert-pentyl, neopentyl, hexyl, or 2-ethylhexyl.

15. The method of claim 14, wherein $R^1$ and $R^2$ are methyl.

16. The method of claim 12, wherein the reacting is carried out at a reactor temperature of 40° C. to 300° C.

* * * * *